United States Patent
Yamada et al.

(10) Patent No.: US 11,793,074 B2
(45) Date of Patent: *Oct. 17, 2023

(54) ORGANIC COMPOUND AND PHOTOELECTRIC CONVERSION ELEMENT

(71) Applicant: CANON KABUSHIKI KAISHA, Tokyo (JP)

(72) Inventors: Naoki Yamada, Inagi (JP); Masumi Itabashi, Yamato (JP); Hironobu Iwawaki, Yokohama (JP); Jun Kamatani, Tokyo (JP); Hiroki Ohrui, Kawasaki (JP); Yosuke Nishide, Kawasaki (JP); Hirokazu Miyashita, Ebina (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 302 days.

This patent is subject to a terminal disclaimer.

(21) Appl. No.: 17/083,731

(22) Filed: Oct. 29, 2020

(65) Prior Publication Data

US 2021/0057653 A1 Feb. 25, 2021

Related U.S. Application Data

(63) Continuation of application No. 16/130,029, filed on Sep. 13, 2018, now Pat. No. 10,868,260.

(30) Foreign Application Priority Data

Sep. 20, 2017 (JP) .................... 2017-180316

(51) Int. Cl.
| | | |
|---|---|---|
| H10K 85/60 | (2023.01) | |
| C07D 209/82 | (2006.01) | |
| H10K 30/30 | (2023.01) | |
| H10K 85/40 | (2023.01) | |
| H10K 85/20 | (2023.01) | |
| H10K 85/30 | (2023.01) | |

(52) U.S. Cl.
CPC ....... *H10K 85/6572* (2023.02); *C07D 209/82* (2013.01); *H10K 30/30* (2023.02); *H10K 30/353* (2023.02); *H10K 85/40* (2023.02); *H10K 85/626* (2023.02); *H10K 85/631* (2023.02); *H10K 85/654* (2023.02); *H10K 85/656* (2023.02); *H10K 85/211* (2023.02); *H10K 85/311* (2023.02); *H10K 85/331* (2023.02); *H10K 85/615* (2023.02); *H10K 85/621* (2023.02); *H10K 85/633* (2023.02); *H10K 85/636* (2023.02); *H10K 85/655* (2023.02)

(58) Field of Classification Search
CPC ............ H01L 51/0067; H01L 51/0072; C07D 209/82; H10K 85/636; H10K 85/654
See application file for complete search history.

(56) References Cited

U.S. PATENT DOCUMENTS

| | | |
|---|---|---|
| 8,378,339 B2 | 2/2013 | Nomura et al. |
| 8,637,860 B2 | 1/2014 | Nomura et al. |
| 8,847,141 B2 | 9/2014 | Fukuzaki et al. |
| 8,847,208 B2 | 9/2014 | Mitsui et al. |
| 9,287,328 B2 | 3/2016 | Suzuki |
| 10,541,260 B2 | 1/2020 | Kamatani et al. |
| 10,868,260 B2 * | 12/2020 | Yamada .............. H01L 51/0094 |

(Continued)

FOREIGN PATENT DOCUMENTS

| | | |
|---|---|---|
| CN | 107778212 A | 3/2018 |
| JP | 2004-323509 A | 11/2004 |

(Continued)

OTHER PUBLICATIONS

KR 2016078765, English translation thereof (Year: 2016).*

(Continued)

*Primary Examiner* — Noble E Jarrell
(74) *Attorney, Agent, or Firm* — VENABLE LLP

(57) ABSTRACT

Provided is an organic compound represented by the general formula [1]:

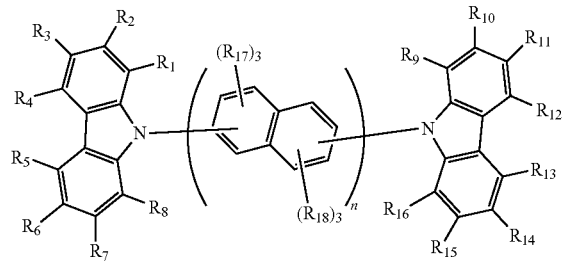

in the formula [1], $R_1$ to $R_{18}$ each represent a hydrogen atom, an alkyl group having 1 or more and 8 or less carbon atoms, an aromatic hydrocarbon group having 6 or more and 18 or less carbon atoms, or an aromatic heterocyclic group having 3 or more and 15 or less carbon atoms, and may be identical to or different from each other, and the plurality of $R_{17}$'s or the plurality of $R_{18}$'s may be identical to or different from each other, and the $R_1$ to the $R_{18}$ may each further have a substituent selected from a halogen atom and an alkyl group having 1 or more and 8 or less carbon atoms, and n represents an integer of 1 or more and 3 or less.

16 Claims, 3 Drawing Sheets

(56) References Cited

U.S. PATENT DOCUMENTS

| | | |
|---|---|---|
| 2006/0088728 A1 | 4/2006 | Kwong et al. |
| 2019/0013469 A1 | 1/2019 | Miyashita et al. |
| 2019/0043926 A1 | 2/2019 | Yamada et al. |
| 2019/0067590 A1 | 2/2019 | Nishide et al. |
| 2019/0119258 A1 | 4/2019 | Nishide et al. |
| 2019/0148644 A1 | 5/2019 | Yamada et al. |

FOREIGN PATENT DOCUMENTS

| | | |
|---|---|---|
| JP | 2010-087488 A | 4/2010 |
| JP | 2011-225544 A | 11/2011 |
| JP | 2013-236008 A | 11/2013 |
| JP | 2017-5249 A | 1/2017 |
| KR | 10-2009-0107208 A | 10/2009 |
| KR | 2010-0025664 A | 3/2010 |
| KR | 10-2011-0014752 A | 2/2011 |
| KR | 10-2016-0078765 A | 7/2016 |
| WO | 2016/181844 A1 | 11/2016 |
| WO | 2017/149958 A1 | 9/2017 |
| WO | 2018/016354 A1 | 1/2018 |

OTHER PUBLICATIONS

Notice of Reasons for Refusal in Japanese Application No. 2017-180316 (dated Nov. 2021).

Notice of Reasons for Refusal in Japanese Application No. 2017-180316 (dated May 2022).

Joseph C. Deaton, "E-Type Delayed Fluorescence of a Phosphine-Supported Cu2(μ-NAr2)2 Diamond Core: Harvesting Singlet and Triplet Excitons in OLEDs," 132(27) J. Am. Chem. Soc. 9499 9508 (Jun. 2010).

Decision of Refusal in Japanese Application No. 2017-180316 (dated Feb. 2023).

\* cited by examiner

ORGANIC COMPOUND AND PHOTOELECTRIC CONVERSION ELEMENT

CROSS-REFERENCE TO RELATED APPLICATIONS

This application is a continuation application of U.S. patent application Ser. No. 16/130,029, filed Sep. 13, 2018, which claims the benefit of Japanese Patent Application No. 2017-180316, filed Sep. 20, 2017. Both prior applications are hereby incorporated by reference herein in their entirety.

BACKGROUND OF THE INVENTION

Field of the Invention

The present invention relates to an organic compound, a photoelectric conversion element using the organic compound, and a photoelectric conversion apparatus, an imaging device, an imaging apparatus each using the photoelectric conversion element.

Description of the Related Art

A planar light-receiving device has been widely used as an imaging device in a camera or the like. The planar light-receiving device is a device obtained by arraying a plurality of pixels each having a photodiode in a two-dimensional manner. When the planar light-receiving device receives light, signals (charges) generated by the photoelectric conversion of the pixels are transferred by using a CCD circuit or a CMOS circuit, and the signals are read out in the light-receiving device or any other member. In addition, a photodiode obtained by forming a photoelectric converter in a semiconductor substrate made of silicon or the like has been known as a photodiode included in a related-art imaging device.

Meanwhile, the development of an element using an organic compound in its photoelectric converter, that is, an organic photoelectric conversion element has been advanced. The organic compound has been expected to enable, for example, an improvement in sensitivity of an imaging device, the thinning and weight reduction thereof, and the flexibilization thereof because of its high extinction coefficient and flexibility.

In such imaging device, a dark current has been known as a cause for the degradation of the quality of an image that has been picked up. In Japanese Patent Application Laid-Open No. 2011-225544 (hereinafter referred to as PTL 1), there is a description that a charge-blocking layer is arranged between a photoelectric conversion layer and an electrode for reducing a dark current in an organic photoelectric conversion element, and hence charge injection from the electrode is suppressed, and there is also a description that Compound a-1 shown below is used in the charge-blocking layer. In addition, in Korean Patent Laid-Open Publication No. 10-2011-0014752 (hereinafter referred to as PTL 2), there is a description that Compound a-2 shown below is used in an organic light-emitting element.

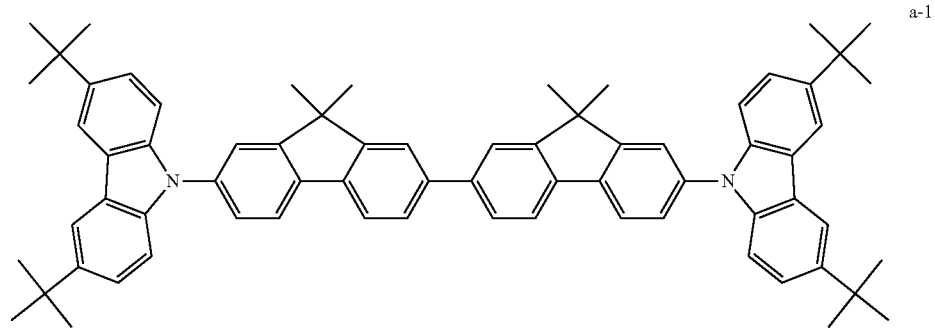

a-1

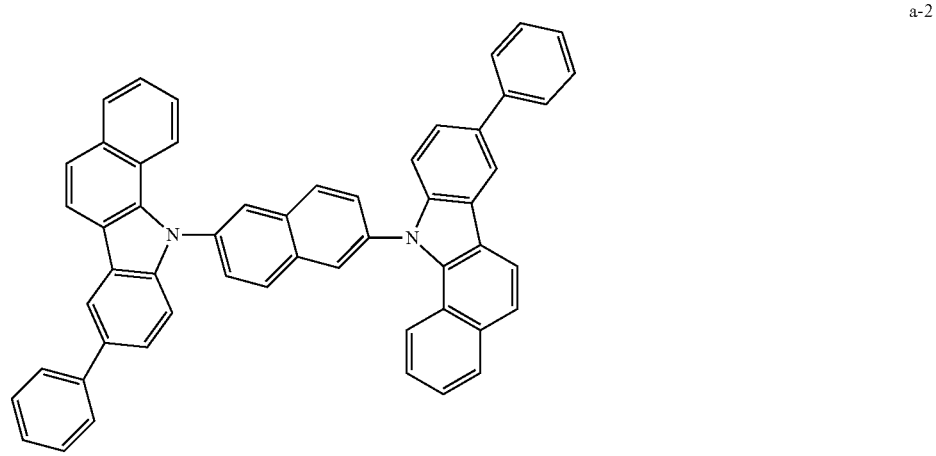

a-2

However, Compound a-1 described in PTL 1 has a high sublimation temperature and hence has involved a problem in that the following risk arises. The compound is decomposed by sublimation, and hence the purity of the compound after the sublimation becomes lower than the purity thereof before the sublimation, and the reduction induces an increase in dark current. In addition, PTL 2 relates to an organic light-emitting element, and hence there is no disclosure of the application of Compound a-2 to a photoelectric conversion element.

The present invention has been made to solve the above-mentioned problem, and an object of the present invention is to provide an organic compound that can be subjected to sublimation purification, that has a low deposition temperature, and that can be suitably used in the organic compound layer of a photoelectric conversion element.

SUMMARY OF THE INVENTION

According to one aspect of the present disclosure, there is provided an organic compound, which is represented by the following general formula [1]:

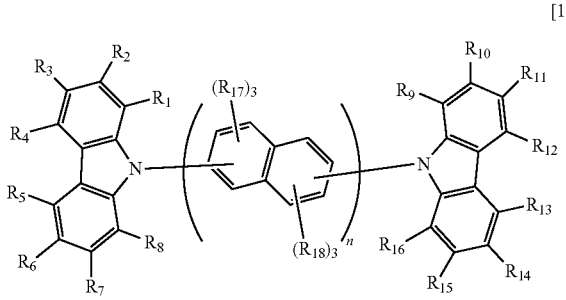

[1]

in the formula [1], $R_1$ to $R_{18}$ each represent a hydrogen atom, an alkyl group having 1 or more and 8 or less carbon atoms, an aromatic hydrocarbon group having 6 or more and 18 or less carbon atoms, or an aromatic heterocyclic group having 3 or more and 15 or less carbon atoms, and may be identical to or different from each other, and the plurality of $R_{17}$'s or the plurality of $R_{18}$'s may be identical to or different from each other, and the $R_1$ to the $R_{18}$ may each further have a substituent selected from a halogen atom and an alkyl group having 1 or more and 8 or less carbon atoms, and n represents an integer of 1 or more and 3 or less, and when the n represents 2 or more, naphthalene units may be identical to or different from each other, and bonding positions of the naphthalene units with adjacent groups may be identical to or different from each other.

Further features of the present invention will become apparent from the following description of exemplary embodiments with reference to the attached drawings.

DESCRIPTION OF THE EMBODIMENTS

Figure 1:
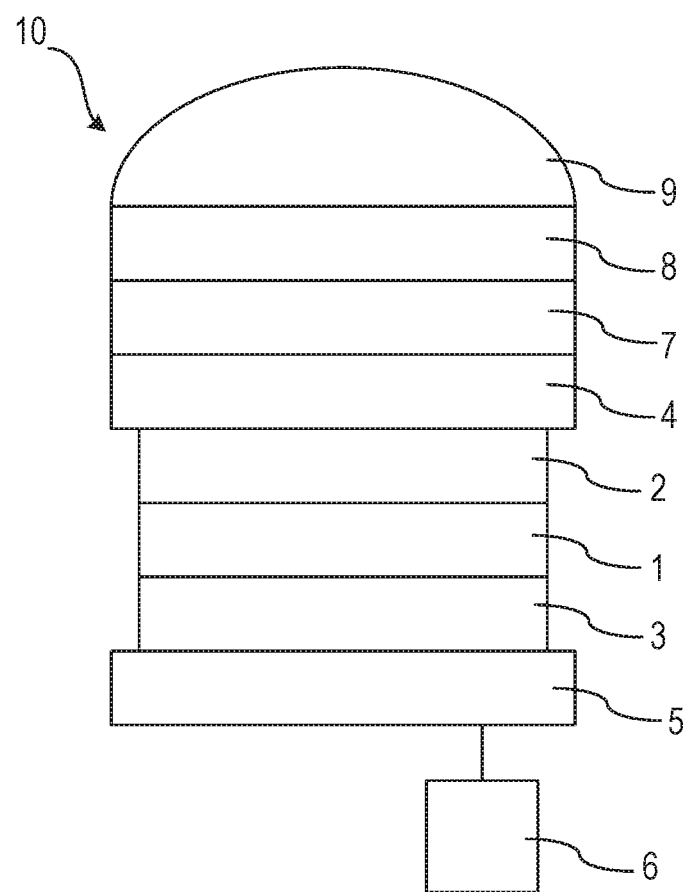
FIG. 1 is a schematic sectional view for illustrating an example of a photoelectric conversion element according to one embodiment.

Preferred embodiments of the present invention will now be described in detail with reference to the accompanying drawings.

Organic Compound According to Embodiment

An organic compound according to this embodiment is represented by the following general formula [1]:

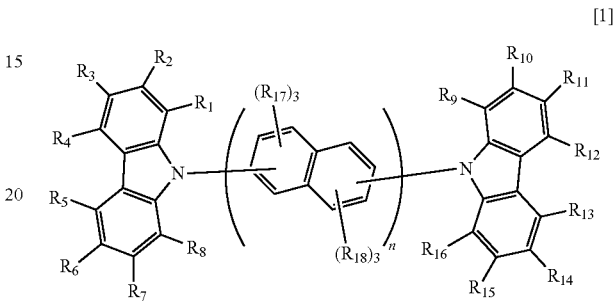

[1]

in the formula [1], $R_1$ to $R_{18}$ each represent a hydrogen atom, an alkyl group having 1 or more and 8 or less carbon atoms, an aromatic hydrocarbon group having 6 or more and 18 or less carbon atoms, or an aromatic heterocyclic group having 3 or more and 15 or less carbon atoms, and may be identical to or different from each other, and the plurality of $R_{17}$'s or the plurality of $R_{18}$'s may be identical to or different from each other, and the $R_1$ to the $R_{18}$ may each further have a substituent selected from a halogen atom and an alkyl group having 1 or more and 8 or less carbon atoms.

Examples of the alkyl group having 1 or more and 8 or less carbon atoms represented by each of the $R_1$ to the $R_{18}$ include a methyl group, an ethyl group, a n-propyl group, an iso-propyl group, a n-butyl group, a sec-butyl group, a tert-butyl group, a n-pentyl group, an iso-pentyl group, a n-hexyl group, a cyclohexyl group, a n-heptyl group, and a n-octyl group. Of those, an iso-propyl group, a sec-butyl group, a tert-butyl group, or an iso-pentyl group is preferred from the viewpoint of sublimability.

Examples of the aromatic hydrocarbon group having 6 or more and 18 or less carbon atoms represented by each of the $R_1$ to the $R_{18}$ include a phenyl group, a biphenyl group, a terphenyl group, a naphthyl group, a phenanthryl group, a fluorenyl group, a chrysenyl group, a triphenylenyl group, and a pyrenyl group. Of those, a substituent having a relatively small molecular weight is preferred from the viewpoint of sublimability. Specifically, a phenyl group or a naphthyl group is preferred.

Examples of the aromatic heterocyclic group having 3 or more and 15 or less carbon atoms represented by each of the $R_1$ to the $R_{18}$ include a pyridyl group, a bipyridyl group, a pyrimidyl group, a quinolyl group, a thiophenyl group, a furanyl group, a dibenzothiophenyl group, and a dibenzofuranyl group. Of those, a substituent having a relatively small molecular weight is preferred from the viewpoint of sublimability. Specifically, a pyridyl group, a thiophenyl group, or a dibenzothiophenyl group is preferred.

Examples of the halogen atom that the $R_1$ to the $R_{18}$ may each have include a fluorine atom, a chlorine atom, a bromine atom, and an iodine atom. Of those, a fluorine atom is preferred.

Examples of the alkyl group having 1 or more and 8 or less carbon atoms that the $R_1$ to the $R_{18}$ may each have include a methyl group, an ethyl group, a n-propyl group, an iso-propyl group, a n-butyl group, a sec-butyl group, a tert-butyl group, a n-pentyl group, a n-hexyl group, a cyclohexyl group, a n-heptyl group, and a n-octyl group. Of those, an iso-propyl group, a sec-butyl group, or a tert-butyl group is preferred.

It is preferred that at least one of the $R_1$ to the $R_{16}$ represents a group except a hydrogen atom, it is more preferred that at least one of the $R_3$, the $R_6$, the $R_{11}$, or the $R_{14}$ represents a group except a hydrogen atom, and it is still more preferred that each of the $R_3$, the $R_6$, the $R_{11}$, and the $R_{14}$ represents a group except a hydrogen atom, because the glass transition temperature of the compound increases. The term "group except a hydrogen atom" as used herein refers to the alkyl group having 1 or more and 8 or less carbon atoms, the aromatic hydrocarbon group having 6 or more and 18 or less carbon atoms, or the aromatic heterocyclic group having 3 or more and 15 or less carbon atoms described above. The group except a hydrogen atom is preferably a bulky alkyl group, such as a t-butyl group, or an aryl group substituted with a bulky alkyl group, such as a t-butylphenyl group, because the glass transition temperature of the compound increases and the sublimation temperature of the compound reduces. Examples of the bulky alkyl group and the aryl group substituted with a bulky alkyl group include an iso-propyl group, a sec-butyl group, a tert-butyl group, a 4-iso-propylphenyl group, a 4-sec-butylphenyl group, and a 4-tert-butylphenyl group. In addition, the group except a hydrogen atom is preferably an alkyl group having 1 or more and 8 or less carbon atoms because the LUMO of the compound becomes shallower (closer to a vacuum level).

n represents an integer of 1 or more and 3 or less. As the n becomes larger, the glass transition temperature increases and hence the compound more easily forms a stable amorphous thin film. Meanwhile, the sublimation purification temperature and deposition temperature of the compound increase. A compound in which the n represents 4 or more has such a property as to be decomposed by sublimation purification or vapor deposition. When the n represents 2 or more, naphthalene units may be identical to or different from each other. In addition, when the n represents 2 or more, the bonding positions of the naphthalene units with adjacent groups may be identical to or different from each other. The bonding positions of a naphthalene unit with adjacent groups, which are not particularly limited, are, for example, 2- and 6-positions, 2- and 7-positions, 1- and 4-positions, or 1- and 5-positions.

Properties of Compound of the Present Invention

The compound of the present invention has the following characteristic properties:
(1) the compound easily forms an amorphous thin film;
(2) the compound has a low sublimation temperature at the time of its sublimation purification or vapor deposition, and hence is hardly decomposed;
(3) the compound has a wide band gap and hence has small absorption in a visible light region; and
(4) the compound has a high ability to block an electron from an electrode and has a high ability to transport a hole from a photoelectric conversion layer.

The properties (1) to (4) are described below.
(1) Compound Easily Forms Amorphous Thin Film
The compound of the present invention has two hole-transportable carbazolyl groups each having high planarity with respect to a naphthalene ring serving as a condensed ring having high rigidity. A carbazolyl group is a hole-transportable substituent having high rigidity because its molecular rotation is fixed as compared to a diarylamino group, such as a diphenylamino group. Thus, the compound of the present invention has a high glass transition temperature and hence easily forms an amorphous thin film.

In order to achieve high external quantum efficiency and a low dark current in an organic photoelectric conversion element, a material that forms a stable and amorphous film is preferably used. This is because when a grain boundary is present in a film, the grain boundary serves as a carrier trap, and hence causes a reduction in photoelectric conversion efficiency and an increase in dark current. In addition, an organic compound layer in contact with an electrode, such as an electron-blocking layer or a hole-blocking layer, is particularly preferably an amorphous thin film. An aggregation state in association with a crystal phase impairs the uniformity of the quality of the film, and hence a local electric field from an electrode may concentrate on the film. Such local electric field concentration causes a leak current and an in-plane variation in sensitivity, and hence reduces the stability of the characteristics of the element.

Further, an organic photoelectric conversion element is required to have thermal stability under high temperature in a mounting process where the element is used as an optical sensor, such as a color filter process or a wire bonding process. Therefore, a material having a high glass transition temperature that can maintain a stable and amorphous film even under high temperature is required as a material for an organic photoelectric conversion element. In consideration of the color filter process or the wire bonding process, the glass transition temperature is preferably 150° C. or more, more preferably 180° C. or more.

(2) Compound has Low Sublimation Temperature at Time of its Sublimation Purification or Vapor Deposition, and Hence is Hardly Decomposed An organic compound to be used in an organic photoelectric conversion element is preferably improved in purity by sublimation purification. This is because when the compound has impurities, a trap or a free carrier derived from the impurities may serve as a cause for a partial leak current or the like to induce an increase in dark current. In addition, in a production process for an organic photoelectric conversion film, the formation of the film by the vacuum deposition of a material therefor is effective in terms of the suppression of the induction of the increase in dark current as in the sublimation purification. However, the decomposition of the compound at the time of its sublimation purification or vapor deposition has the opposite effect because impurities are produced by the decomposition at the time of the film formation.

In order to design a molecule having a high glass transition temperature, in the case of a hole-transportable material, a condensed polycyclic group to which an amino group is bonded needs to be made rigid and increased in molecular weight. However, the design increases the sublimation temperature or deposition temperature of the compound, and the sublimation temperature or the deposition temperature becomes higher than the decomposition temperature of the compound in some cases. Accordingly, a contrivance, such as the selection of an appropriate condensed polycyclic group, is needed.

The compound of the present invention has the following feature: the compound has a high glass transition temperature, and hence is not decomposed by its sublimation purification or vapor deposition. The glass transition temperatures, sublimation temperatures, results of purity analysis by high performance liquid chromatography (HPLC) before and after sublimation, and decomposition properties after the sublimation of Compound A-6 of the present invention and Comparative Compound a-1 having a central skeleton different from that of Compound A-6 are shown in Table 1. Each of both the compounds has a glass transition temperature of 200° C. or more, which is such a glass transition temperature that the compound can withstand high temperature in a mounting process where the compound is used as an optical sensor, such as a color filter production process or a wire bonding process. Meanwhile, Compound A-6 of the present invention has a low sublimation temperature, and hence the compound after its sublimation is not decomposed. However, Comparative Compound a-1 has a high sublimation temperature, and hence the purity of the compound after its sublimation becomes lower than the purity thereof before the sublimation, and the compound is decomposed by the sublimation. As can be seen from the foregoing, a naphthylene group is used in the compound of the present invention, and hence the compound has a sufficiently high glass transition temperature and its sublimation temperature can be reduced to such an extent that the compound is not decomposed.

The glass transition temperatures were evaluated by differential scanning calorimetry (DSC). The sublimation temperatures were each determined as follows: the sublimation purification of each of the compounds was started by slowly increasing the temperature thereof while flowing argon at a degree of vacuum of 1×10-1 Pa at the time of the sublimation purification, and the temperature at which a sufficient sublimation rate was achieved was defined as the sublimation temperature. In addition, methanol was used as an eluent in the HPLC, and a peak was detected with UV light having a wavelength of 254 nm.

(3) Compound has Wide Band Gap and Hence has Small Absorption in Visible Light Region In order to achieve high external quantum efficiency in an organic photoelectric conversion element, a larger quantity of light needs to reach its photoelectric conversion layer. For example, when an electron-blocking layer positioned in a light incident direction has absorption in the visible light region, the quantity of light that reaches the photoelectric conversion layer reduces, and hence the external quantum efficiency reduces. Accordingly, the electron-blocking layer is preferably formed of a material having small absorption in the visible light region. Meanwhile, in order for the electron-blocking layer to sufficiently suppress electron injection from an electrode, the thickness of the layer is preferably larger. When the thickness is not sufficiently large, there is a risk in that tunnel-type electron injection occurs at the time of the application of a voltage to the layer, or that unevenness or foreign matter on the surface of the electrode cannot be sufficiently covered, and hence a physical short circuit or a leak current occurs. In addition, when the layer is a thin film, the film hardly becomes a uniform film, and hence the photoelectric conversion layer and the electrode are locally close to each other. Accordingly, an electric field may concentrate on the portion where the layer and the electrode are close to each other to cause charge injection from the electrode. Accordingly, a material having the following feature is preferred as a material forming a charge-blocking layer: even when the material is formed into a film having a sufficiently large thickness, the film has small absorption in the visible light region and hence does not reduce the quantity of light that reaches the photoelectric conversion layer.

The compound of the present invention includes a naphthylene group and a carbazolyl group each having a short absorption wavelength, and hence provides a material having small absorption in the visible light region. Calculated values for the S1s of Compound b-1 of the present invention in which a naphthylene group is substituted with a carbazolyl group and Comparative Compound b-2 in which a

TABLE 1

| | Glass transition temperature (° C.) | Sublimation temperature (° C.) | HPLC Purity (%) Before sublimation/ after sublimation | Decomposition property after sublimation |
|---|---|---|---|---|
| A-6 | 201 | 370 | 99.90/99.97 | Not decomposed |
| a-1 | 208 | 400 | 99.25/99.06 | Decomposed | naphthylene group is substituted with a benzocarbazolyl group by molecular orbital calculation are shown in Table 2. It is found that the S1 of Comparative Compound b-2 has absorption at a wavelength longer than that of the S1 of Compound b-1 of the present invention.

(4) Compound has High Ability to Block Electron from Electrode and has High Ability to Transport Hole from Photoelectric Conversion Layer In order to achieve high external quantum efficiency in an organic photoelectric conversion element, a charge gener-

TABLE 2

| | Calculated value for S1 (nm) |
|---|---|
| b-1 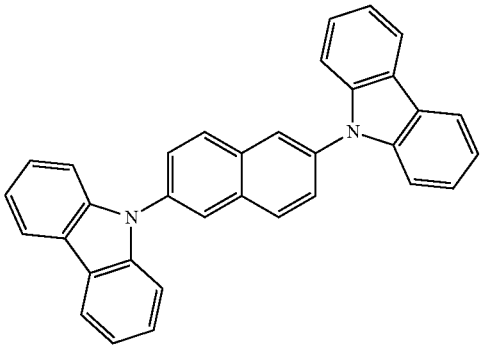 [SMILES: c1ccc2c(c1)c1ccccc1n2-c1ccc2cc(-n3c4ccccc4c4ccccc43)ccc2c1] | 383 |
| b-2 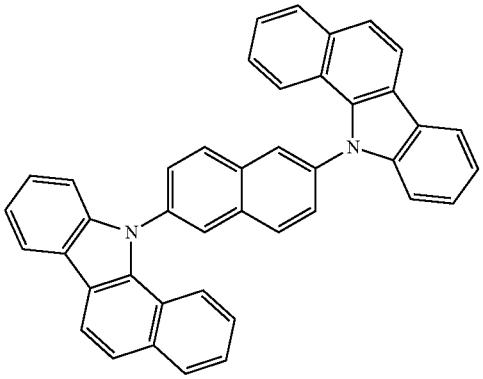 [SMILES: c1ccc2c(c1)ccc1c3ccccc3n(-c3ccc4cc(-n5c6ccccc6c6ccc7ccccc7c65)ccc4c3)c21] | 419 |

Density functional theory (DFT) widely used at present was used as a calculation approach for molecular orbital calculation. B3LYP was used as a functional and 6-31G* was used as a basis function. The molecular orbital calculation was performed through use of Gaussian 09 widely used at present (Gaussian 09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford CT, 2010.).

ated in its photoelectric conversion layer needs to be immediately transported to its collecting electrode. For example, a hole generated in the photoelectric conversion layer reaches a hole-collecting electrode through an electron-blocking layer. Therefore, the electron-blocking layer preferably has a HOMO level equal to or shallower (closer to the vacuum level) than that of a material that transports a hole generated in the photoelectric conversion layer, and preferably has a high hole mobility. The compound of the present invention has carbazolyl groups each excellent in hole-transporting ability at both of its ends. Accordingly, the compound is a material having a high hole-transporting ability, and hence can be suitably used as the electron-blocking layer of the organic photoelectric conversion element. In order to suppress charge injection from an electrode and reduce a dark current in the organic photoelectric conversion element, an injection barrier between the electrode and a charge-blocking layer needs to be sufficiently large. For example, the LUMO level of the electron-blocking layer is preferably shallow (close to the vacuum level) in order that electron injection from the hole-collecting electrode may be sufficiently suppressed. Calculated values for the HOMOs and LUMOs of Compound b-1 of the present invention and Comparative Compound b-2 by molecular orbital calculation are shown in Table 3.

As can be seen from the foregoing, the compound of the present invention is a compound having the properties (1) to

TABLE 3

| | HOMO (eV) | LUMO (eV) |
|---|---|---|
| b-1 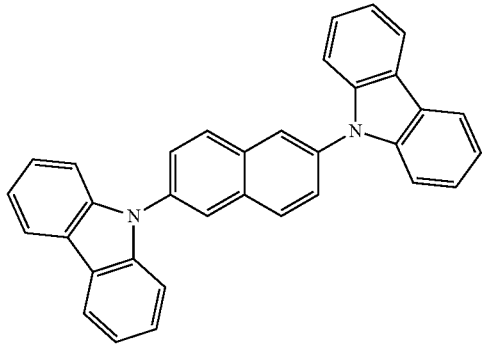 [SMILES: c1ccc2c(c1)c1ccccc1n2-c1ccc2cc(-n3c4ccccc4c4ccccc43)ccc2c1] | −5.30 | −1.52 |
| b-2 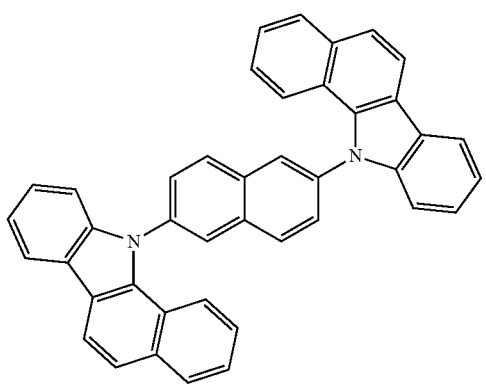 [SMILES: c1ccc2c(c1)ccc1c3ccccc3n(-c3ccc4cc(-n5c6ccccc6c6ccc7ccccc7c65)ccc4c3)c21] | −6.43 | −1.72 |

The HOMO of Comparative Compound b-2 is extremely deep (distant from the vacuum level) as compared to that of Compound b-1 of the present invention, and the HOMO of Compound b-1 of the present invention is shallow (close to the vacuum level). In the case where Comparative Compound b-2 is used as the electron-blocking layer, when the HOMO of the material that transports a hole generated in the photoelectric conversion layer is shallow, the generated hole cannot be blocked and swept out to the electrode, and hence the external quantum efficiency may be low. Meanwhile, the LUMO of Comparative Compound b-2 is extremely deep (distant from the vacuum level) as compared to that of Compound b-1 of the present invention, and the LUMO of Compound b-1 of the present invention is shallow (close to the vacuum level). In the case where Compound b-1 of the present invention is used as the electron-blocking layer, the electron injection from the electrode is suppressed and hence the dark current may be low.

(4), and hence can be suitably used in a photoelectric conversion element as compared to Comparative Compounds a-1 and b-2. In particular, the compound of the present invention can be suitably used in an electron-blocking layer. In addition, when the compound of the present invention is used as the organic compound layer of the photoelectric conversion element, a spin coating method may be adopted as a method of forming a layer containing the compound of the present invention, but vapor deposition under a vacuum (vacuum deposition method) is preferably utilized. This is because the utilization of the vacuum deposition method can form a high-purity thin film.

Specific Examples of Compound of the Present Invention

Specific examples of the compound of the present invention are shown below. However, the compound of the present invention is not limited to these specific examples.

A-1
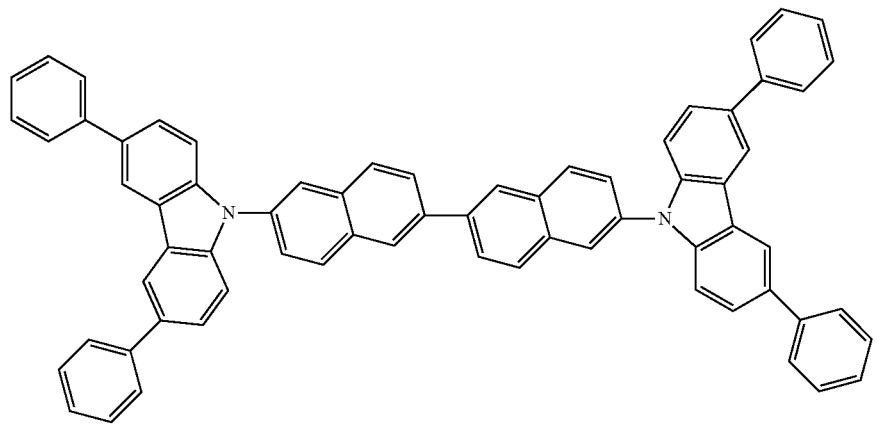
A-2
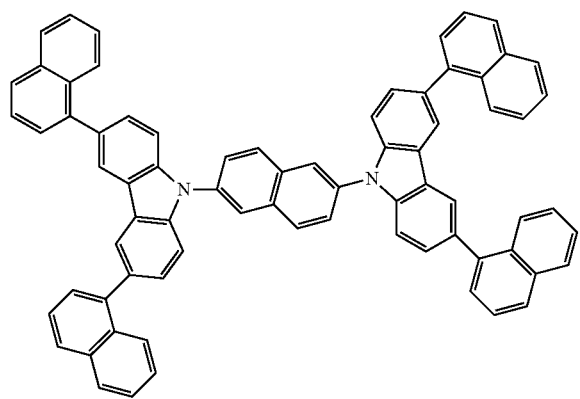
A-3
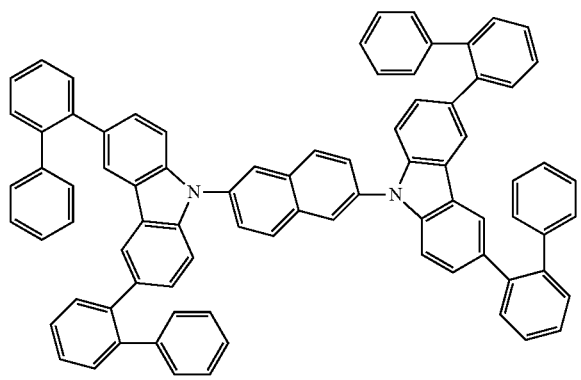
A-4
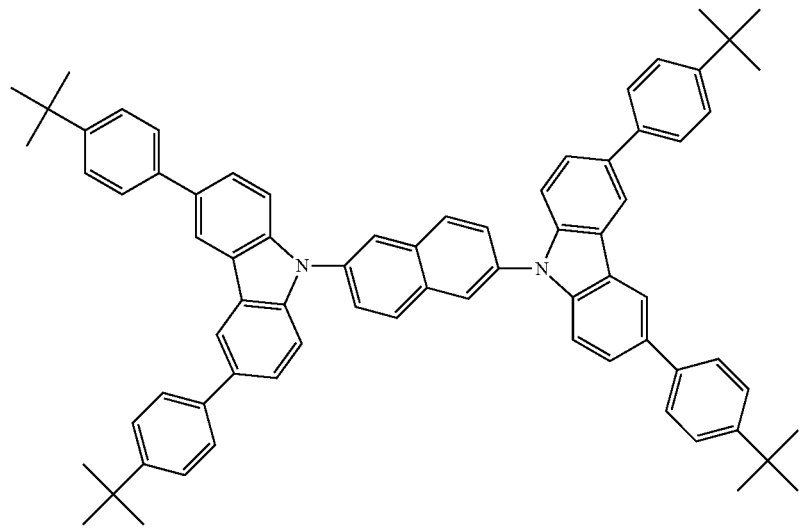

-continued
A-5
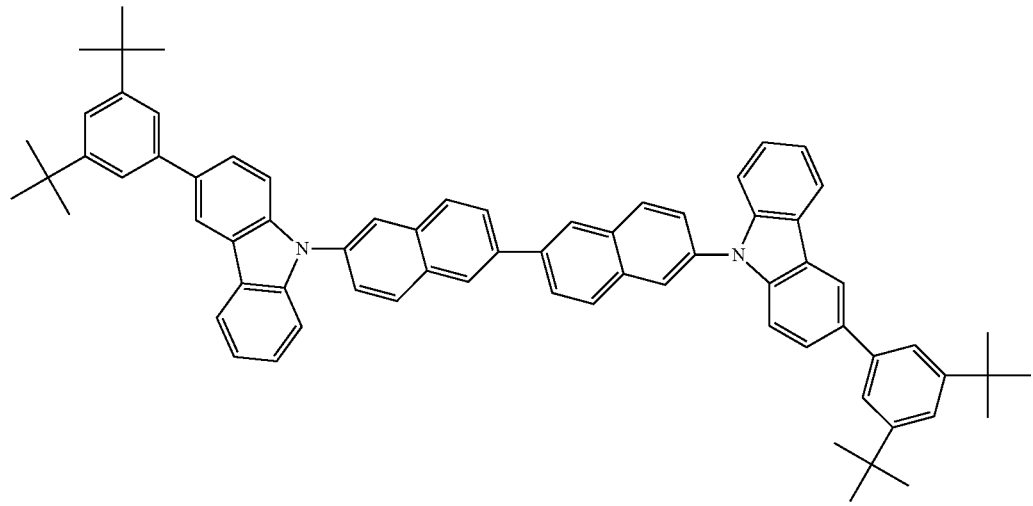
A-6
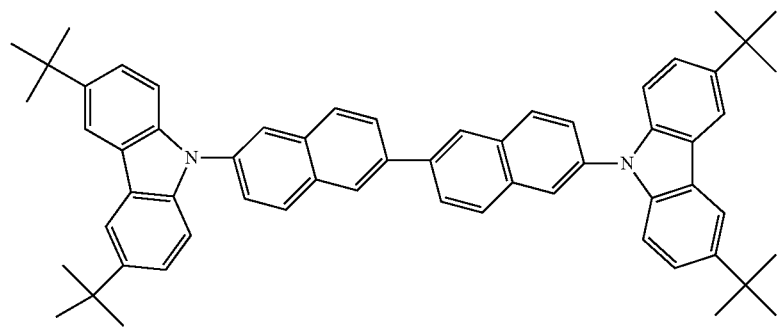
A-7
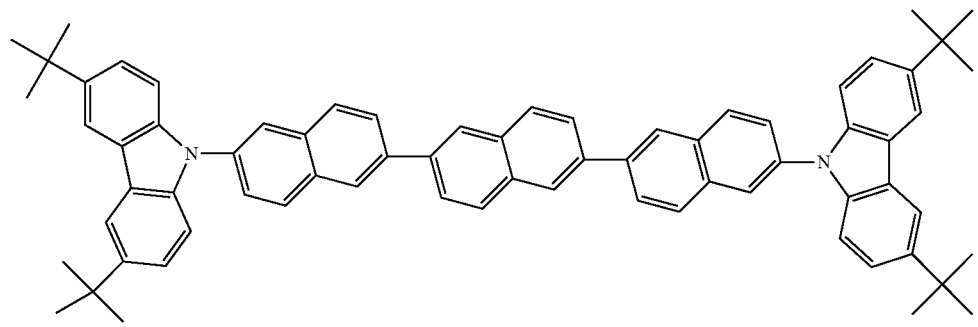
A-8
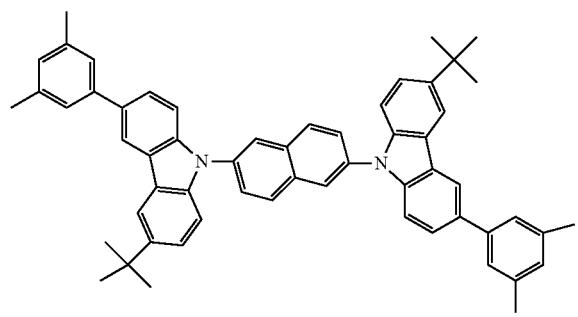
A-9
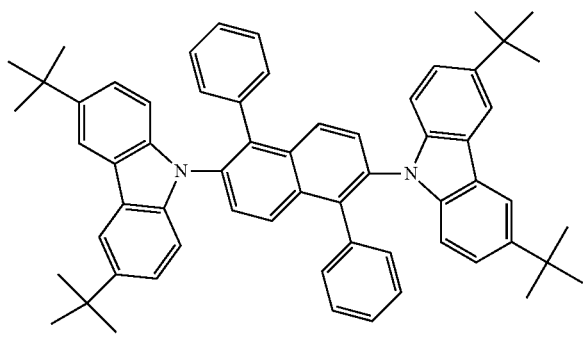

-continued
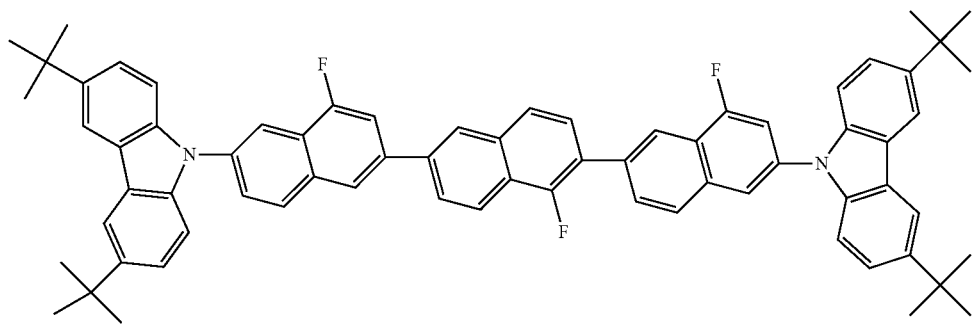
A-10
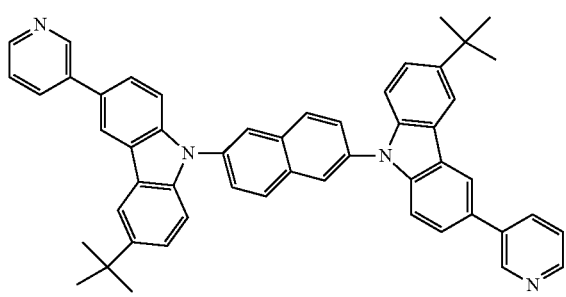
A-11
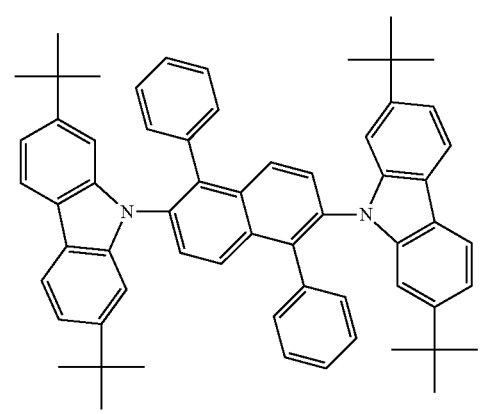
A-12
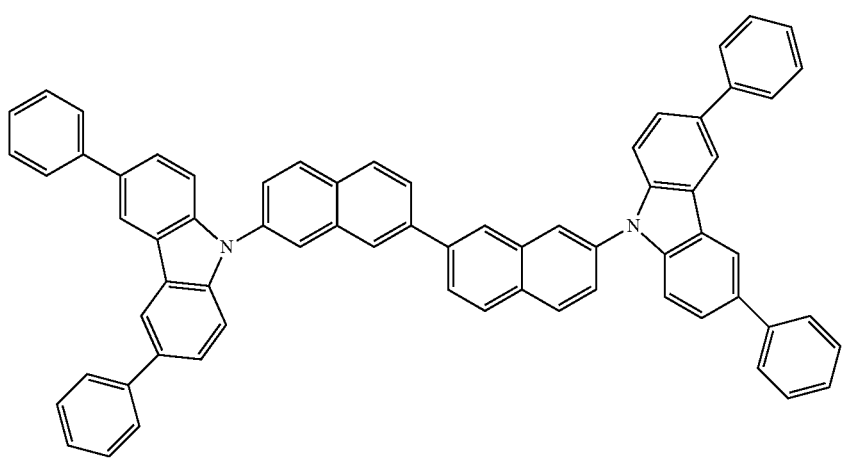
B-1

-continued
B-2
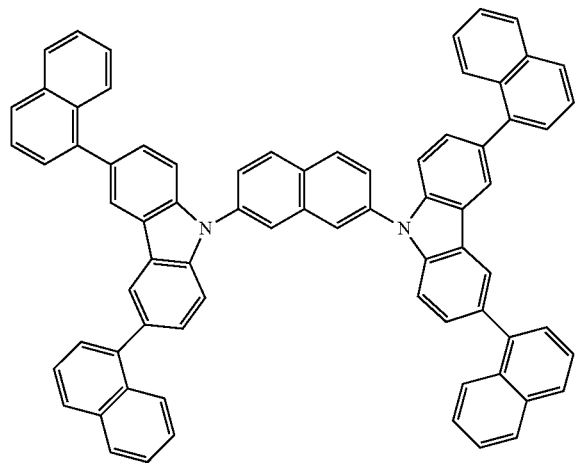
B-3
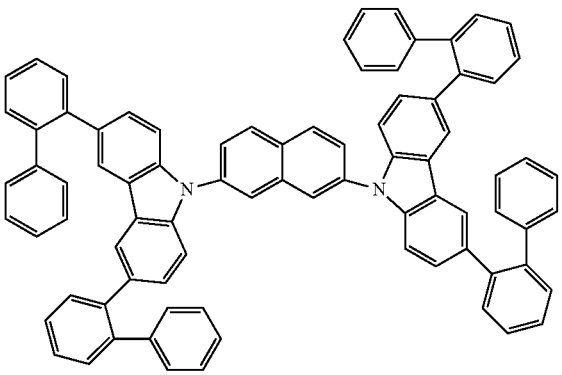
B-4
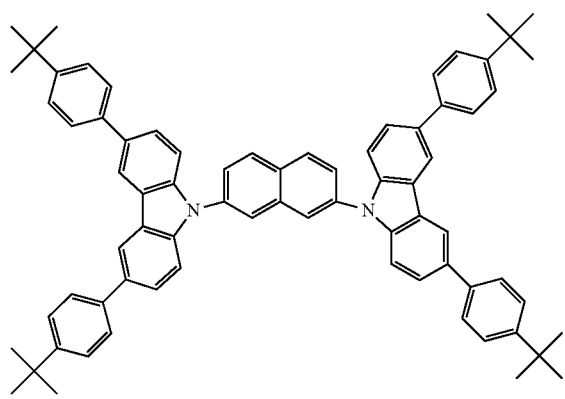
B-5
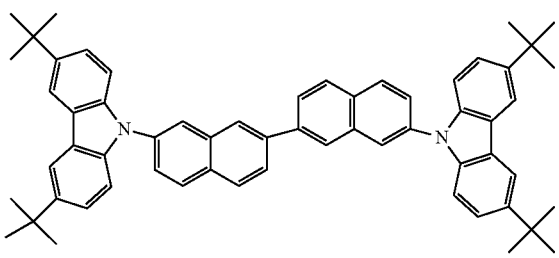
B-6
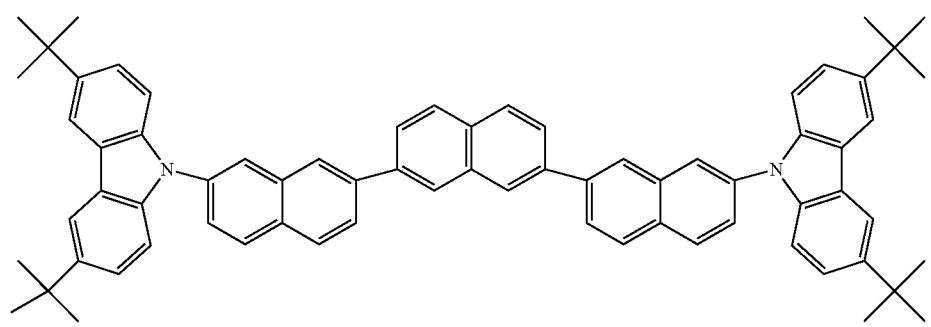

-continued
B-7
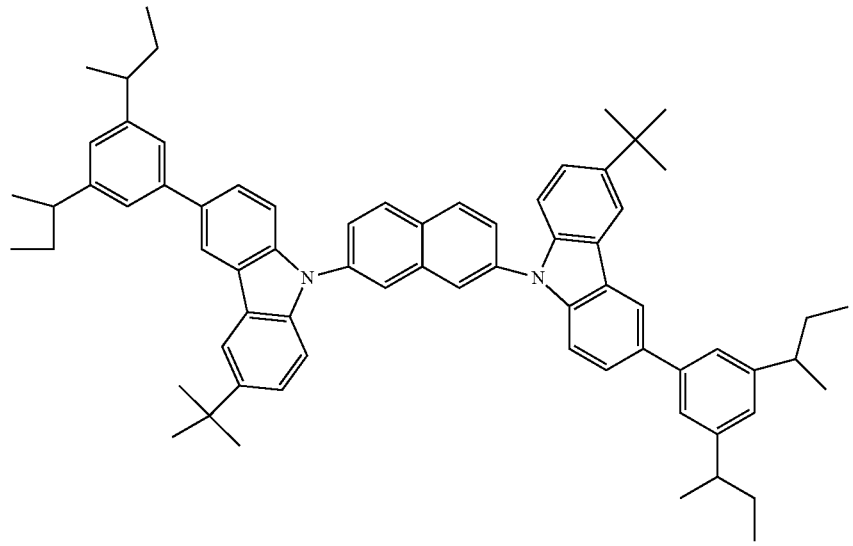
B-8
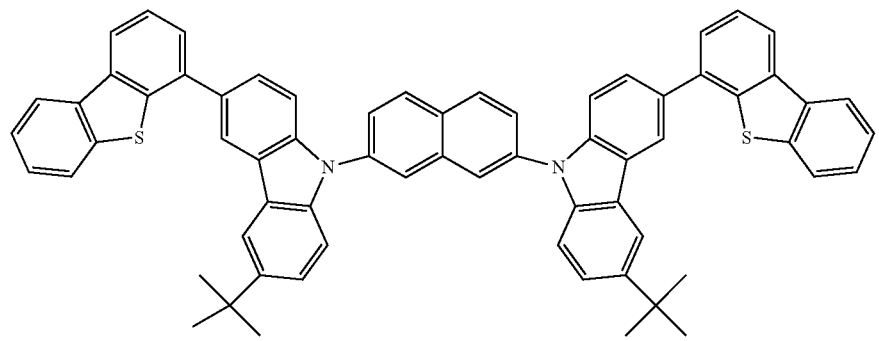
B-9
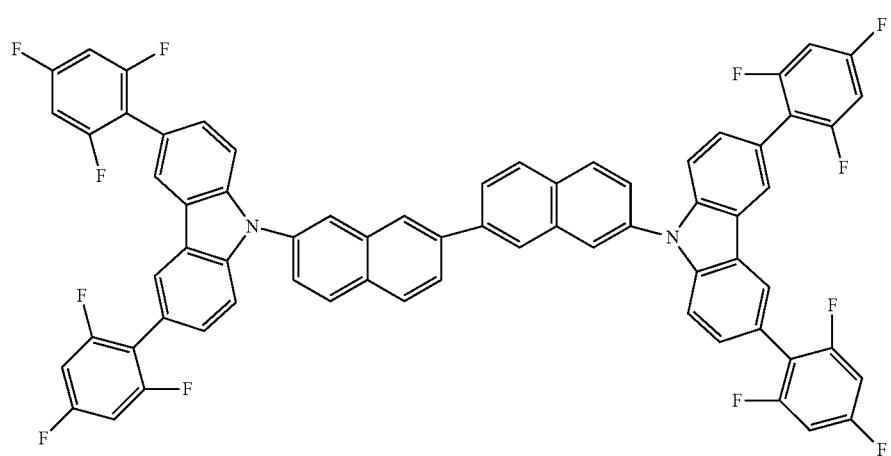

-continued
C-1
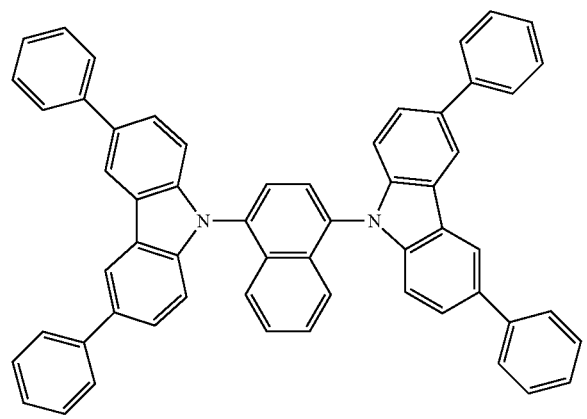
C-2
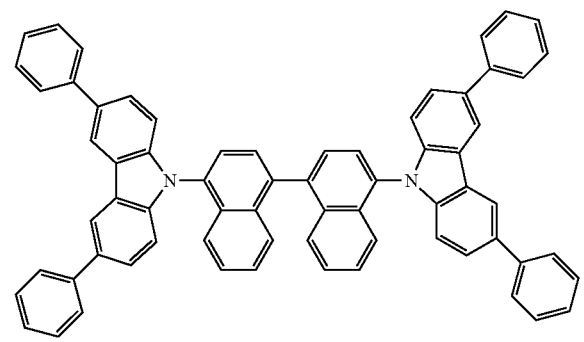
C-3
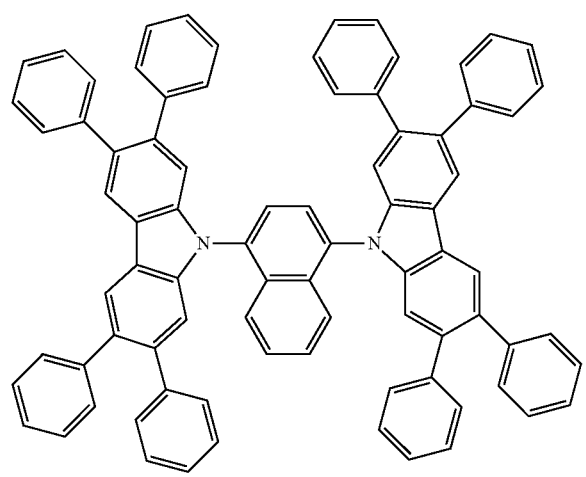
C-4
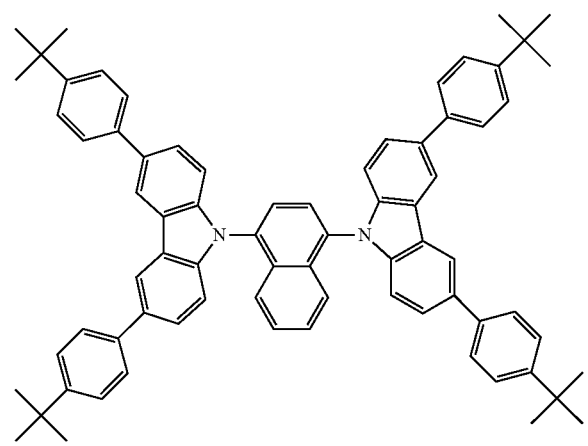
C-5
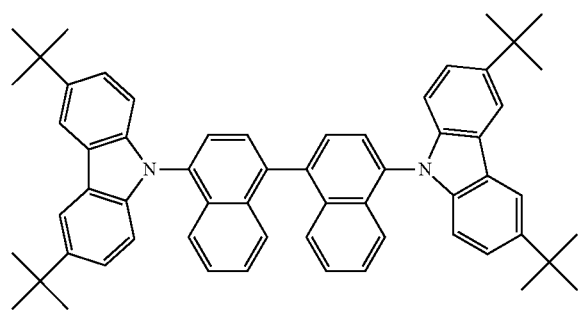

C-6
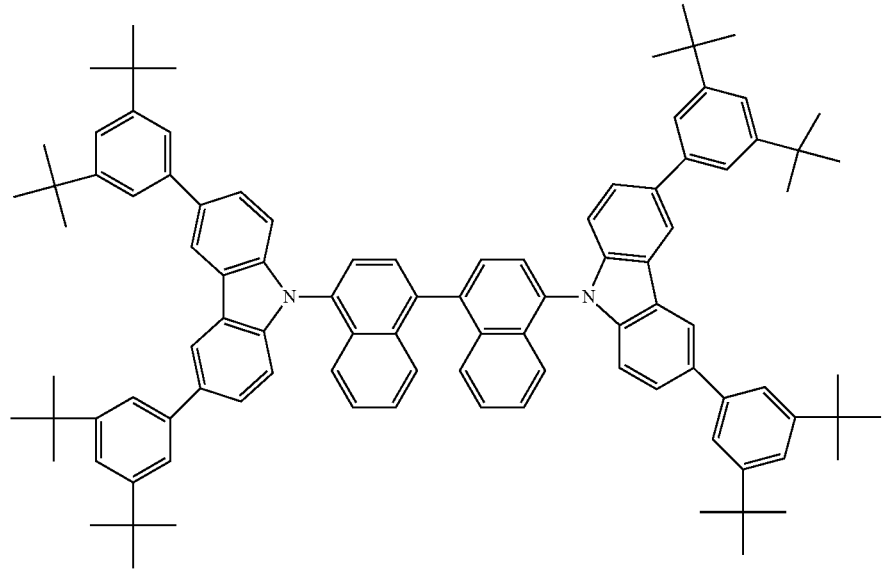
C-7
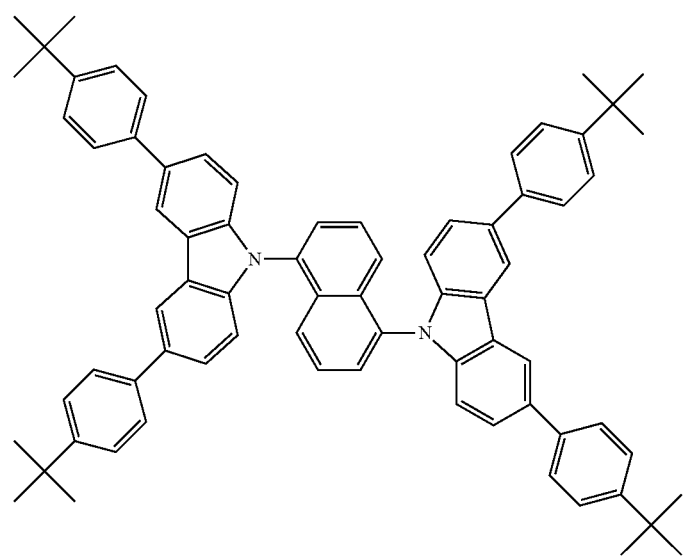
C-8
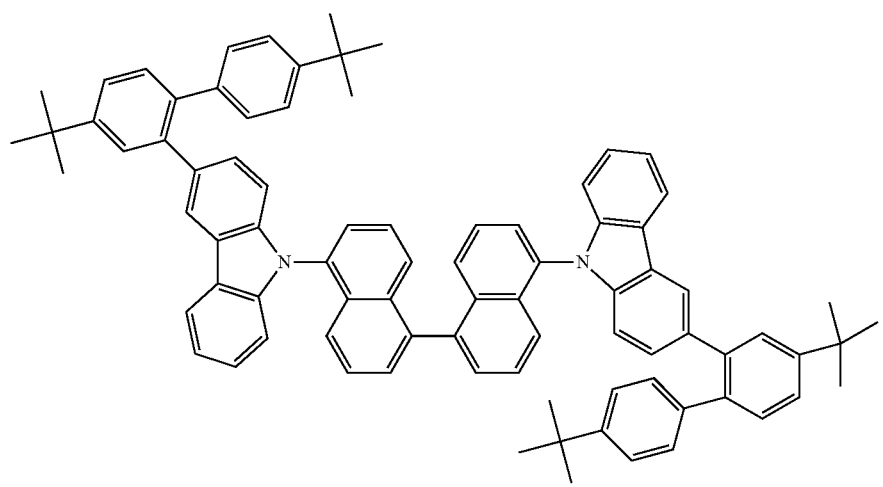

-continued
C-9
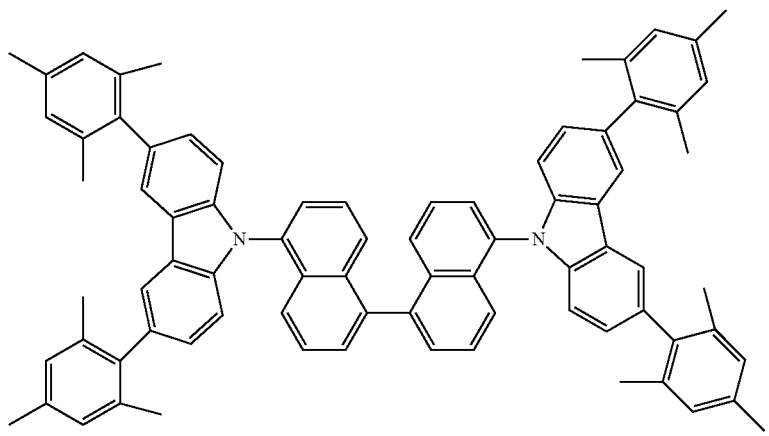
D-1
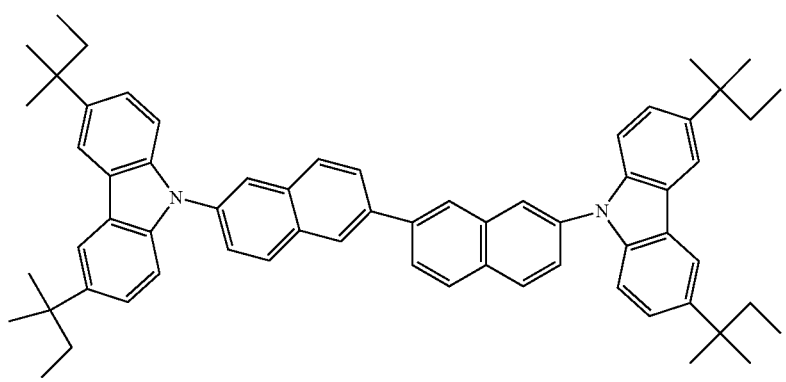
D-2
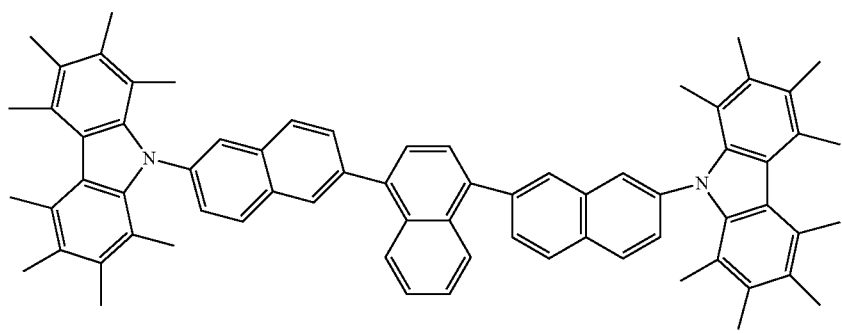
D-3
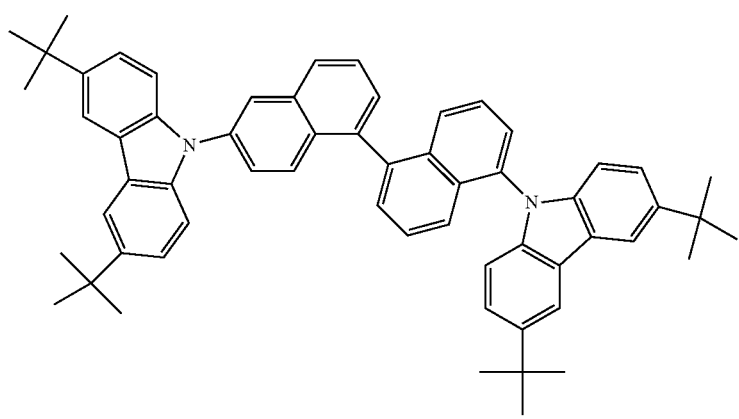

The compounds corresponding to the group A are compounds in each of which a carbazolyl group or an adjacent naphthylene group is bonded to the 2- or 6-position of a naphthylene group in the formula [1]. Each of the compounds has high planarity, and hence has a short intermolecular distance and a high mobility in a film.

The compounds corresponding to the group B are compounds in each of which a carbazolyl group or an adjacent naphthylene group is bonded to the 2- or 7-position of a naphthylene group in the formula [1]. Each of the compounds has a wide band gap and high planarity, and hence has a short intermolecular distance and a high mobility in a film.

The compounds corresponding to the group C are compounds in each of which a carbazolyl group or an adjacent naphthylene group is bonded to the 1- or 4-position, or 1- or 5-position of a naphthylene group in the formula [1]. Each of the compounds has a structure in which a naphthylene group and a carbazolyl group are twisted by an influence of steric hindrance, and hence is reduced in intermolecular stacking, has a low sublimation temperature, and forms a stable and highly amorphous organic compound layer that hardly crystallizes.

The compounds corresponding to the group D are compounds in each of which the respective naphthylene groups are different from each other in position to be bonded to a carbazolyl group or an adjacent naphthylene group. Each of the compounds has low molecular symmetry, and hence forms a stable and highly amorphous organic compound layer that hardly crystallizes.

Photoelectric Conversion Element According to Embodiment (1) Photoelectric Conversion Element A photoelectric conversion element according to this embodiment includes an anode, a cathode, and an organic compound layer arranged between the anode and the cathode, and the organic compound layer has a layer containing the organic compound of the present invention. FIG. 1 is a schematic sectional view for illustrating an example of the photoelectric conversion element according to the embodiment. In a photoelectric conversion element 10, an organic compound layer is arranged between an anode 5 and a cathode 4, and the organic compound layer has a first organic layer 1. The first organic layer 1 is a layer configured to form a photoelectric conversion portion configured to convert light into charge. In view of the foregoing, the first organic layer 1 can also be referred to as "photoelectric conversion layer." When the photoelectric conversion element 10 has a plurality of layers, the plurality of layers are preferably laminated in a direction from the anode 5 to the cathode 4. The organic compound layer may have: a second organic layer 2 arranged between the first organic layer 1 and the cathode 4; and a third organic layer 3 arranged between the first organic layer 1 and the anode 5. A protective layer 7, a wavelength-selecting portion 8, and a lens 9 are arranged on the cathode 4. A readout circuit 6 is connected to the anode 5. The photoelectric conversion element 10 may be formed on a substrate (not shown). When the photoelectric conversion element 10 performs photoelectric conversion, a voltage may be applied between the anode 5 and the cathode 4. The voltage is preferably about 1 V or more and about 15 V or less, though the preferred voltage varies depending on the total thickness of the organic compound layer. The voltage is more preferably about 2 V or more and about 10 V or less.

(2) Substrate

The photoelectric conversion element according to the embodiment may include a substrate. Examples of the substrate include a glass substrate, a flexible substrate, and a semiconductor substrate.

As described above, the photoelectric conversion element according to the embodiment may include a semiconductor substrate. A constituent element for the semiconductor substrate is not limited as long as a charge-storing portion and a floating diffusion (FD) can be formed by the injection of impurities. Examples thereof include Si, GaAs, and GaP. Of those, Si is particularly preferred. The semiconductor substrate may be an N-type epitaxial layer. In that case, a P-type well, an N-type well, a P-type semiconductor region, and an N-type semiconductor region are arranged on the semiconductor substrate.

The charge-storing portion is an N-type semiconductor region or P-type semiconductor region formed on the semiconductor substrate by ion implantation, and is a region configured to store charge generated in the photoelectric conversion portion. When an electron is stored, the N-type semiconductor region may be formed on the surface of the semiconductor substrate, or a storage diode of a PN structure may be formed from the surface of the substrate. In each case, an electron can be stored in the N-type semiconductor region. Meanwhile, when a hole is stored, the P-type semiconductor region may be formed on the surface of the semiconductor substrate, or a storage diode of an NP structure may be formed from the surface of the substrate. In each case, an electron can be stored in the P-type semiconductor region.

The stored charge is transferred from the charge-storing portion to the FD. The charge transfer may be controlled by a gate electrode. The charge generated in the first organic layer 1 is stored in the charge-storing portion, and the charge stored in the charge-storing portion is transferred to the FD. After that, the charge is converted into a current by an amplification transistor (FIG. 2) to be described later. In addition, when the charge-storing portion forms a PN junction, the photoelectric conversion may be performed by light leaking from the photoelectric conversion portion. The photoelectric conversion element may include a charge-outputting portion without including the charge-storing portion. When the element includes the outputting portion, the charge generated in the first organic layer 1 is transferred from an electrode to the amplification transistor or the like without through the FD.

(3) Anode (Electron-Collecting Electrode) 5 and Cathode (Hole-Collecting Electrode) 4

The anode 5 is an electrode configured to collect an electron out of the charge generated in the first organic layer 1. The anode may be a pixel electrode in the construction of an imaging device. The anode 5 may be arranged on a side closer to a pixel circuit with respect to the cathode 4. The anode 5 can be called an electron-collecting electrode because of its function. A constituent material for the anode 5 is, for example, ITO, indium zinc oxide, $SnO_2$, antimony-doped tin oxide (ATO), ZnO, Al-doped zinc oxide (AZO), gallium-doped zinc oxide (GZO), $TiO_2$, or fluorine-doped tin oxide (FTO).

The cathode 4 is an electrode configured to collect a hole out of the charge generated in the first organic layer 1. The cathode may be a pixel electrode in the construction of the imaging device. A constituent material for the cathode 4 is, for example, a metal, a metal oxide, a metal nitride, a metal boride, an organic conductive compound, or a mixture obtained by combining two or more kinds thereof. Specific examples thereof include: conductive metal oxides, such as antimony-doped or fluorine-doped tin oxide (ATO or FTO), tin oxide, zinc oxide, indium oxide, indium tin oxide (ITO), and indium zinc oxide; metal materials, such as gold, silver, magnesium, chromium, nickel, titanium, tungsten, and aluminum; conductive compounds, such as oxides or nitrides of these metal materials (e.g., titanium nitride (TiN)); mixtures or laminates of these metals and the conductive metal oxides; inorganic conductive substances, such as copper iodide and copper sulfide; organic conductive materials, such as polyaniline, polythiophene, and polypyrrole; and laminates of these substances or materials and ITO or titanium nitride. The constituent material for the cathode 4 is particularly preferably a material selected from the group consisting of an alloy of magnesium and silver, titanium nitride, molybdenum nitride, tantalum nitride, and tungsten nitride.

The pixel electrode may be any one of the anode 5 and the cathode 4. The transparency of an electrode on a light extraction side is preferably high. The transparency is specifically 80% or more. In addition, an electrode on a light incident side can also be referred to as "upper electrode." In that case, the other electrode is referred to as "lower electrode."

A method of forming each of the above-mentioned two kinds of electrodes (the anode and the cathode) can be appropriately selected in consideration of its suitability with an electrode material to be used. Specifically, the electrodes can be formed by, for example, a printing system, a wet system, such as a coating system, a physical system, such as a vacuum deposition method, a sputtering method, or an ion plating method, or a chemical system, such as CVD or a plasma CVD method. In the case where the electrodes are formed by using ITO, the electrodes can be formed by a method such as an electron beam method, the sputtering method, a resistance heating deposition method, a chemical reaction method (e.g., a sol-gel method), or the application of a dispersed product of indium tin oxide. In addition, in such case, the surfaces of the formed electrodes (ITO electrodes) may be subjected to, for example, a UV-ozone treatment or a plasma treatment. In the case where the electrodes are formed by using TiN, various film-forming methods typified by a reactive sputtering method can be used. In addition, in such case, the formed electrodes (TiN electrodes) may be subjected to, for example, an annealing treatment, the UV-ozone treatment, or the plasma treatment.

(4) First Organic Layer (Photoelectric Conversion Layer) 1

As described above, the first organic layer 1 can also be referred to as "photoelectric conversion layer." A constituent material for the first organic layer 1 of the photoelectric conversion element according to the embodiment is described. It is preferred that the first organic layer 1 have a high light absorptivity and perform the charge separation of received light efficiently, that is, have high photoelectric conversion efficiency. In addition, the layer is preferably capable of immediately transporting generated charge, that is, an electron and a hole to the electrodes. In addition, in order that a reduction in quality of the layer, such as crystallization, may be suppressed, a material having a high glass transition temperature is preferred. The layer may be a mixed layer of the organic compound and the material having a high glass transition temperature from the viewpoint of an improvement in quality thereof. The first organic layer 1 may contain a plurality of kinds of organic compounds. When the first organic layer 1 contains a plurality of kinds of organic compounds, the plurality of kinds of organic compounds may be mixed in one layer, or the plurality of kinds of organic compounds may be incorporated into a plurality of layers.

The first organic layer 1 is preferably a layer containing an organic p-type compound, such as a p-type organic semiconductor, or an organic n-type compound, such as an n-type organic semiconductor, and more preferably includes a bulk hetero layer (mixed layer), which is obtained by mixing the organic p-type compound and the organic n-type compound, in at least part thereof. When the first organic layer 1 has the bulk hetero layer, its photoelectric conversion efficiency (sensitivity) can be improved. When the layer has the bulk hetero layer at an optimum mixing ratio, the electron mobility and hole mobility of the first organic layer 1 can be increased, and hence the optical response speed of the photoelectric conversion element can be increased.

The first organic layer 1 preferably contains a fullerene, a fullerene analog, or a fullerene derivative as an n-type organic semiconductor. The fullerene, the fullerene analog, and the fullerene derivative are hereinafter sometimes collectively referred to as "fullerene group." An electron path is formed by a plurality of fullerene group molecules, and hence the electron transportability of the layer is improved and the responsiveness of the photoelectric conversion element is improved. When the total amount of the photoelectric conversion layer is defined as 100%, the content of the fullerene group is preferably 20 mass % or more and 80 mass % or less. The fullerene or the fullerene analog is a generic term for closed-shell cavity-shaped clusters each including only many carbon atoms, and examples thereof include fullerene C60, and fullerenes C70, C74, C76, and C78 serving as higher order fullerenes. Those materials may be used alone or in combination thereof. A material to be used as a material responsible for charge separation and electron carriage is not limited to the fullerene group, and a plurality of other materials may be simultaneously used. A material except the fullerene group is, for example, a naphthalene compound, such as NTCDI, a perylene compound, such as PTCDI, a phthalocyanine compound, such as SubPc, or a thiophene compound, such as DCV3T, the compounds being known as n-type organic semiconductors.

Examples of the fullerene or the fullerene analog include fullerene C60, fullerene C70, fullerene C76, fullerene C78, fullerene C80, fullerene C82, fullerene C84, fullerene C90, fullerene C96, fullerene C240, fullerene C540, mixed fullerene, and fullerene nanotubes. Examples of the fullerene derivative include the following.

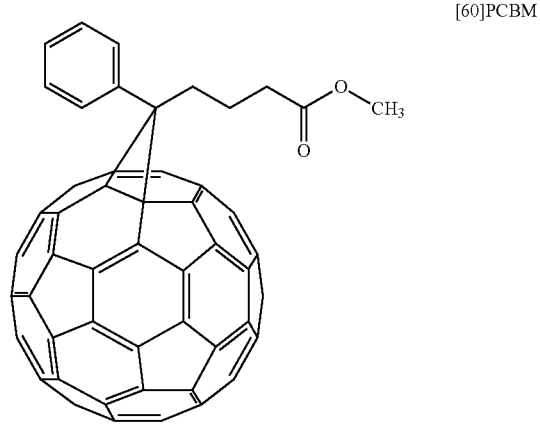

[60]PCBM bis[60]PCBM
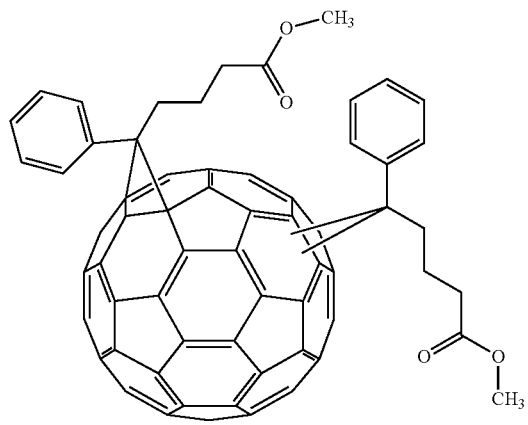
[70]PCBM
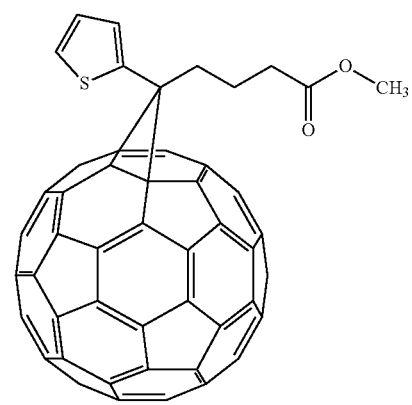
[60]TbCBM
CG1
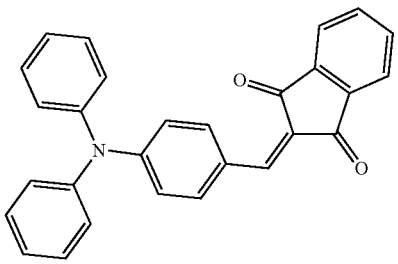
CG2
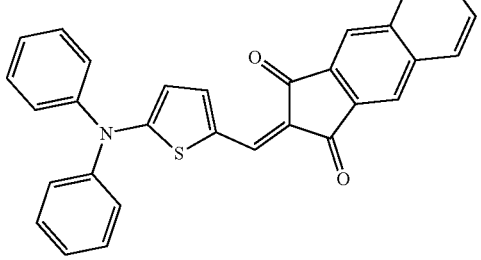
CG3
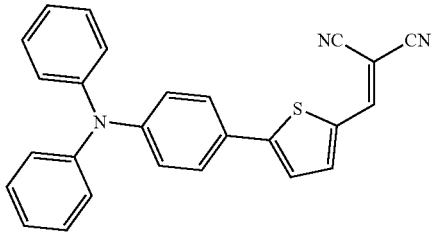
CG4
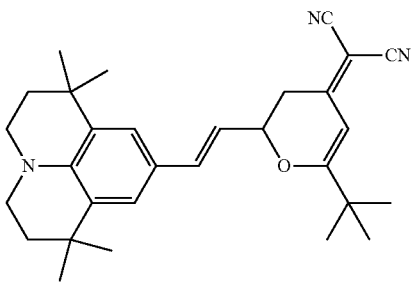
CG5
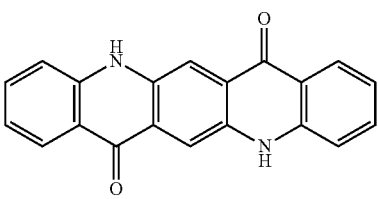
CG6
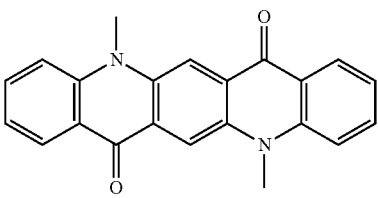
Examples of the p-type organic semiconductor may include the following organic compounds. The compounds shown below may have substituents, such as an alkyl group, to the extent that their functions are not impaired.

-continued
CG7
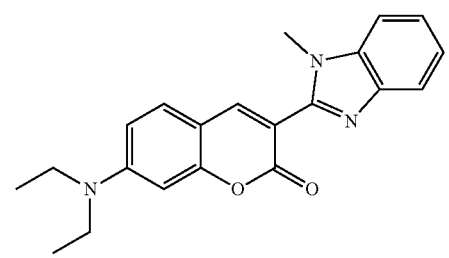
CG8
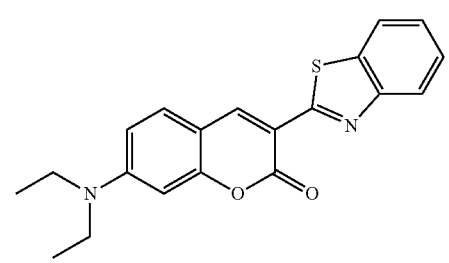
CG9
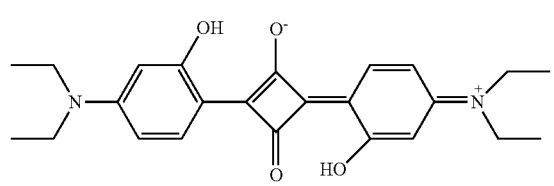
CG10
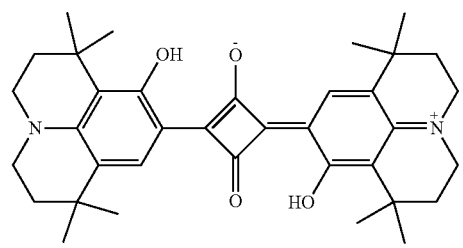
CG11
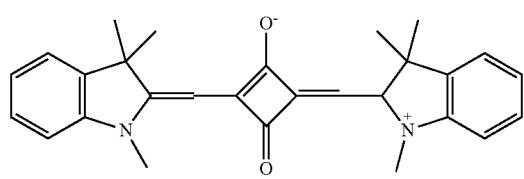
CG12
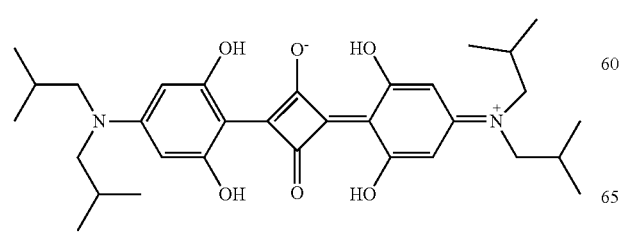
-continued
CG13
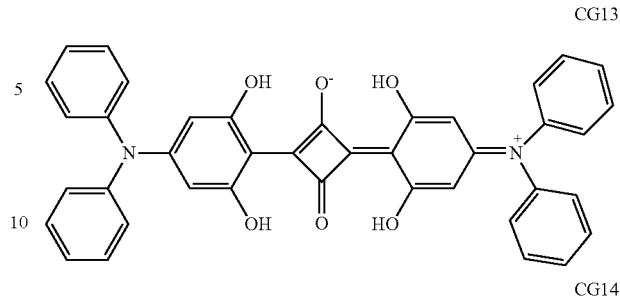
CG14
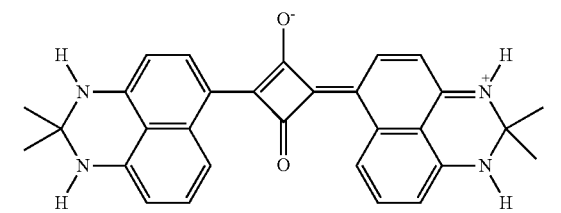
CG15
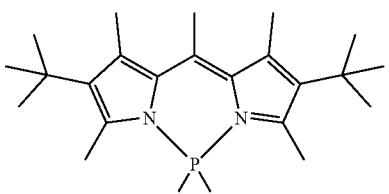
CG16
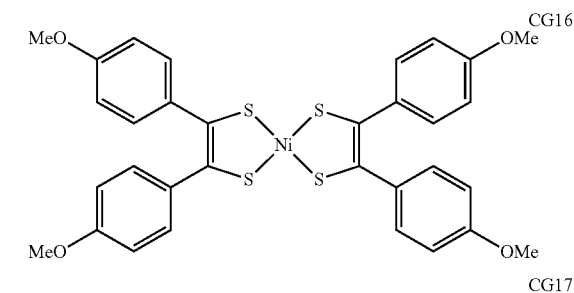
CG17
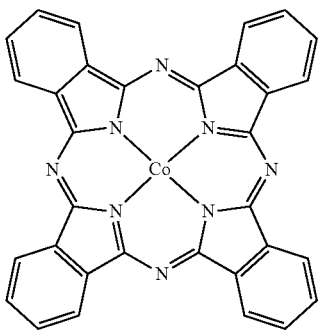
CG18
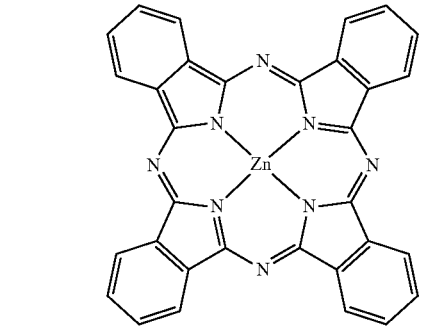

CG19
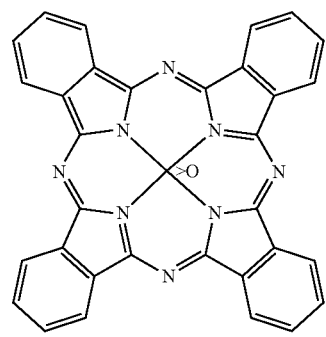
CG20
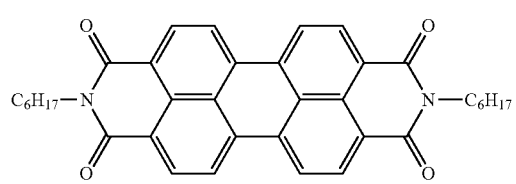
CG21
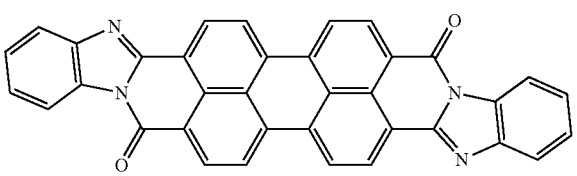
CG22
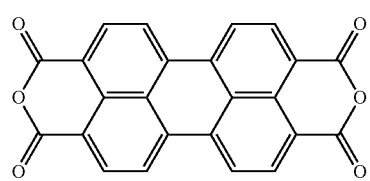
CG23
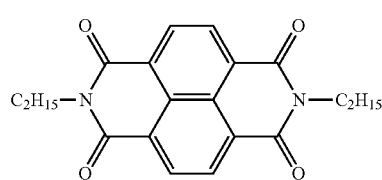
CG24
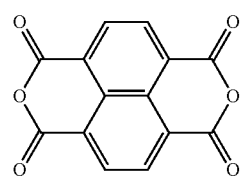
CG25
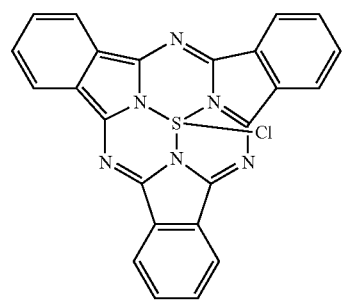
CG26
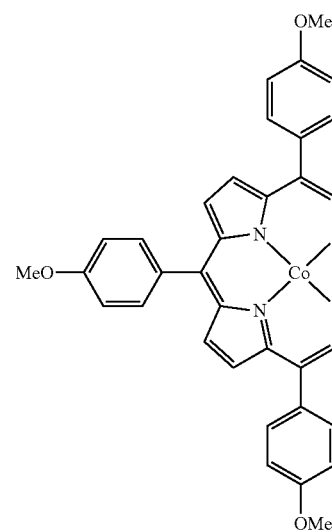
CG27
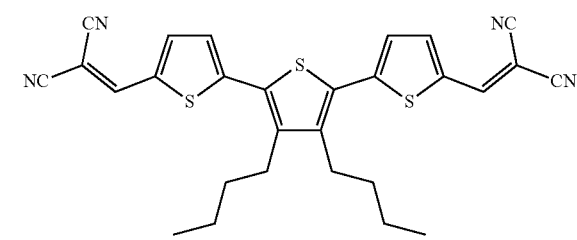
CG28
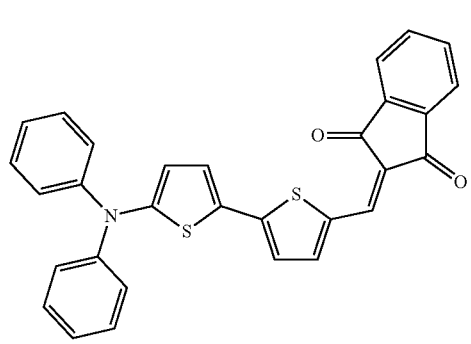
CG29
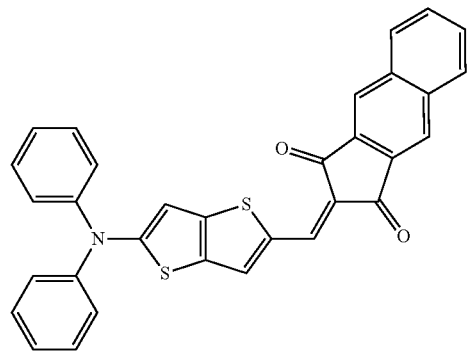

-continued

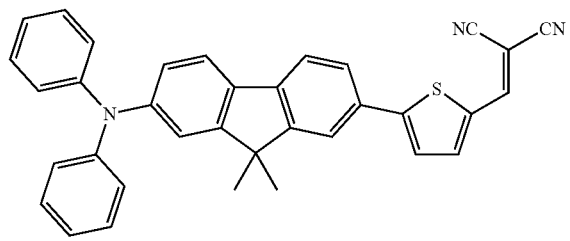
CG30

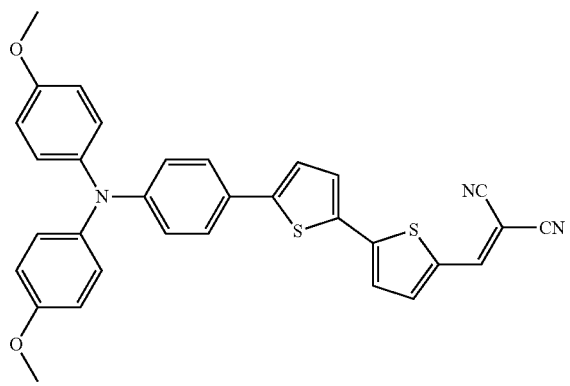
CG31

(5) Second Organic Layer (Electron-Blocking Layer) 2

The second organic layer 2 is a layer configured to suppress the flow of an electron from the cathode 4 into the first organic layer 1, and preferably has a small electron affinity (LUMO close to a vacuum level). A small electron affinity can be rephrased as a low LUMO. The second organic layer 2 can be called an electron-blocking layer because of its function. The second organic layer 2 is preferably the layer having the organic compound of the present invention. The second organic layer 2 may be a plurality of layers, or a bulk hetero layer (mixed layer) may be used as the layer. The cathode 4 and the second organic layer 2 may be in contact with each other, or the photoelectric conversion element may include any other functional layer therebetween.

(6) Third Organic Layer (Hole-Blocking Layer) 3

The third organic layer 3 is a layer configured to suppress the flow of a hole from the anode 5 into the first organic layer 1, and preferably has a large ionization potential (HOMO distant from the vacuum level). A large ionization potential can be rephrased as a high HOMO. The third organic layer 3 can be called a hole-blocking layer because of its function. The third organic layer 3 may be a plurality of layers, or a bulk hetero layer (mixed layer) may be used as the layer. The photoelectric conversion element may include any other functional layer between the anode 5 and the third organic layer 3.

Next, a constituent material for the third organic layer 3 is described. The third organic layer 3 preferably has a high ionization potential in order that the injection of a hole from the anode 5 into the first organic layer 1 may be prevented. In addition, in order that an electron generated in the first organic layer 1 may be immediately transported to the anode 5, a material having a high electron mobility is preferred. In addition, in order that a reduction in quality of the layer, such as crystallization, may be suppressed, a material having a high glass transition temperature is preferred. From the viewpoint of an improvement in quality thereof, the layer may be a mixed layer of the material having a high electron mobility and the material having a high glass transition temperature. Specifically, the layer may be a mixed layer of the material having a high electron mobility and the compound of the present invention. Specific examples of a compound to be used as a hole-blocking material are shown below, but the compound is of course not limited thereto.

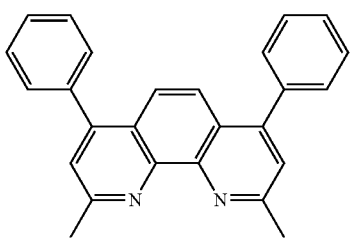
HB1

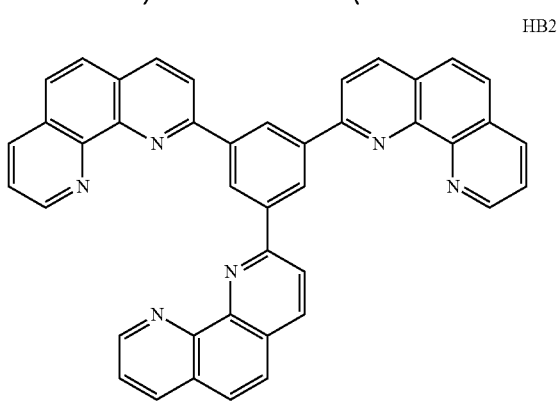
HB2

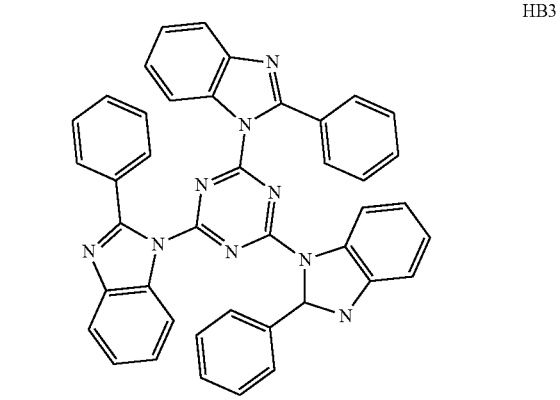
HB3

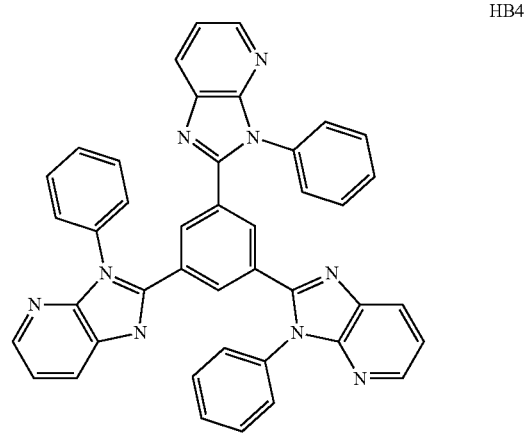
HB4

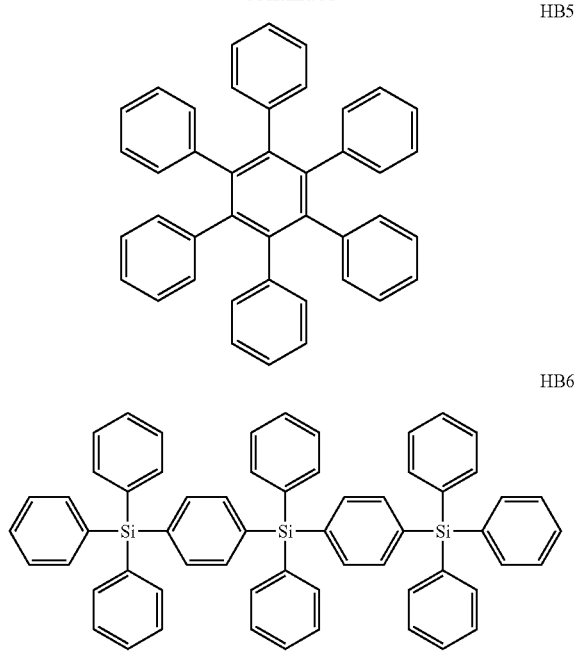

HB5

HB6

In addition to the foregoing compounds, a fullerene group known as an n-type organic semiconductor can also be suitably used. As described above, the fullerene group is a material excellent in electron transportability, and hence can be used as a constituent material for the hole-blocking layer.

(7) Protective Layer 7

The protective layer 7 is a layer to be formed above the electrodes, and is preferably an insulating layer. The protective layer 7 may be formed of a single material, or may include a plurality of materials. When the layer includes a plurality of materials, the layer may be obtained by laminating a plurality of layers, or may be a layer obtained by mixing the plurality of materials. A constituent material for the protective layer 7 is, for example, an organic material, such as a resin, or an inorganic material, such as silicon nitride, silicon oxide, or aluminum oxide. The layer can be formed by, for example, sputtering or an atomic layer deposition method (ALD method). Silicon nitride is also described as SiNX and silicon oxide is also described as SiOX. X is a numerical value representing an element ratio.

A planarization layer may be arranged on the protective layer 7. The layer is arranged for preventing the wavelength-selecting portion 8 from being affected by the surface state of the protective layer 7. The planarization layer can be formed by, for example, a known production method, application method, or vacuum deposition method. The layer may be produced by performing, for example, CMP as required. A constituent material for the planarization layer is, for example, an organic material, such as a resin, or an inorganic material, such as SiNX, SiOX, or Al2O3, and may include an organic compound or a mixture of such material and compound. Examples of a formation method for the layer may include the same methods as those for the protective layer 7.

(8) Wavelength-Selecting Portion 8

The wavelength-selecting portion 8 is arranged on the planarization layer. When the photoelectric conversion element does not include the planarization layer, the portion is arranged on the protective layer 7. The wavelength-selecting portion 8 can be arranged on the light incident side of the photoelectric conversion element. Examples of the wavelength-selecting portion 8 include a color filter, a scintillator, and a prism. The color filter is a filter configured to transmit light having a predetermined wavelength in a quantity larger than that of light having any other wavelength. For example, the element can correspond to the entirety of the visible light region by using three kinds of color filters, that is, R, G, and B color filters. When the three kinds of color filters, that is, the R, G, and B color filters are used, a Bayer array, a delta array, or the like may be used as the arrangement of the color filters. In addition, the wavelength-selecting portion may be a prism configured to separate only light having a predetermined wavelength. The position at which the wavelength-selecting portion 8 is arranged is not limited to the position illustrated in FIG. 1. The wavelength-selecting portion 8 only needs to be arranged at any position on an optical path from an object or a light source to the photoelectric conversion layer 1.

(9) Lens 9

The lens 9, such as a microlens, is an optical member for converging light from the outside in the first organic layer 1. Although a hemispherical lens is illustrated in FIG. 1, the shape of the lens is not limited thereto. The lens 9 includes, for example, quartz, silicon, or an organic resin. The shape and material of the lens are not limited as long as its light convergence is not inhibited.

(10) Other Construction

The photoelectric conversion element may include any other photoelectric conversion element on an electrode. When the other photoelectric conversion element is a photoelectric conversion element configured to perform the photoelectric conversion of light having a wavelength different from that of light to be subjected to photoelectric conversion by the foregoing element, the light having the different wavelength can be detected at an identical or substantially identical in-plane position on the substrate.

In addition, the photoelectric conversion element may be constructed as follows: the element further includes another kind of organic compound layer configured to perform the photoelectric conversion of light having a wavelength different from that of light to be subjected to photoelectric conversion by the first organic layer 1, and the first organic layer 1 and the other kind of organic compound layer are laminated. With the construction, as in the construction in which the photoelectric conversion elements are laminated, the light having the different wavelength can be detected at an identical position or a substantially identical position on the substrate.

Photoelectric Conversion Apparatus According to Embodiment

A photoelectric conversion apparatus of the present invention includes a plurality of kinds of photoelectric conversion elements configured to receive light beams having different wavelengths. At least one kind of photoelectric conversion element out of the plurality of kinds of photoelectric conversion elements is the photoelectric conversion element of the present invention, and the plurality of kinds of photoelectric conversion elements are laminated.

Imaging Device According to Embodiment and Imaging Apparatus Including the Device (1) Imaging Device The photoelectric conversion element according to the embodiment can be used in an imaging device. The imaging device includes: a plurality of photoelectric conversion elements serving as light-receiving pixels; a readout circuit connected to each of the photoelectric conversion elements; and a signal processing circuit (signal processing portion) connected to the readout circuit. Information based on charge that has been read out is transmitted to the signal processing portion connected to the imaging device. Examples of the signal processing portion include a CMOS sensor and a CCD sensor. When pieces of information acquired in the respective light-receiving pixels are gathered in the signal processing portion, an image can be obtained.

The imaging device may include a plurality of photoelectric conversion elements, and the plurality of photoelectric conversion elements may have color filters different from each other in kind. The plurality of kinds of color filters are color filters configured to transmit light beams having wavelengths different from each other. Specifically, the elements may have the respective R, G, and B color filters. The plurality of photoelectric conversion elements may include a photoelectric conversion layer as a common layer. The term "common layer" means that the photoelectric conversion layer of a photoelectric conversion element and the photoelectric conversion layer of a photoelectric conversion element adjacent thereto are one and the same.

Figure 2:
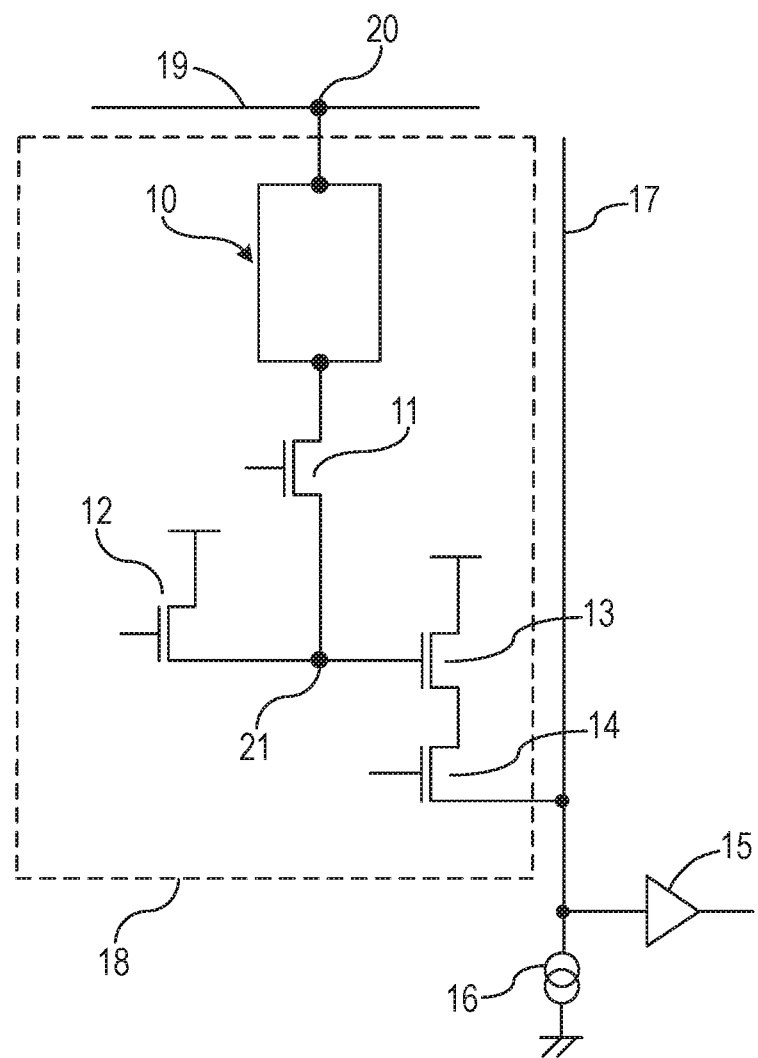
FIG. 2 is a circuit diagram of a pixel including the photoelectric conversion element according to one embodiment.

FIG. 2 is a circuit diagram of a pixel including the photoelectric conversion element according to the embodiment. The photoelectric conversion element 10 is connected to a common wiring 19 by a node A 20. The common wiring 19 may be connected to the ground. A pixel 18 may include the photoelectric conversion element 10 and a readout circuit for reading out a signal produced in the photoelectric conversion portion. The readout circuit may include, for example, a transfer transistor 11, an amplification transistor 13, a selection transistor 14, and a reset transistor 12. The transfer transistor 11 is electrically connected to the photoelectric conversion element 10. The amplification transistor 13 has a gate electrode electrically connected to the photoelectric conversion element 10. The selection transistor 14 is configured to select a pixel from which information is read out. The reset transistor 12 is configured to supply a reset voltage to the photoelectric conversion element.

Transfer by the transfer transistor 11 may be controlled by a gate voltage. The supply of the reset voltage by the reset transistor 12 may be controlled by a voltage to be applied to its gate. The selection transistor 14 is brought into a selection or non-selection state by its gate voltage. The transfer transistor 11, the reset transistor 12, and the amplification transistor 13 are connected to each other by a node B 21. The readout circuit may be free of the transfer transistor 11 depending on its construction. The reset transistor 12 is a transistor configured to supply a voltage configured to reset the potential of the node B 21. The application of a signal to the gate of the reset transistor 12 can control the supply of the voltage. The circuit may be free of the reset transistor 12 depending on the construction. The amplification transistor 13 is a transistor configured to flow a current in accordance with the potential of the node B 21. The amplification transistor 13 is connected to the selection transistor 14 configured to select the pixel 18 from which a signal is output. The selection transistor 14 is connected to a current source 16 and a column output portion 15, and the column output portion 15 is connected to the signal processing portion. The selection transistor 14 is connected to a vertical output signal line 17. The vertical output signal line 17 is connected to the current source 16 and the column output portion 15.

Figure 3:
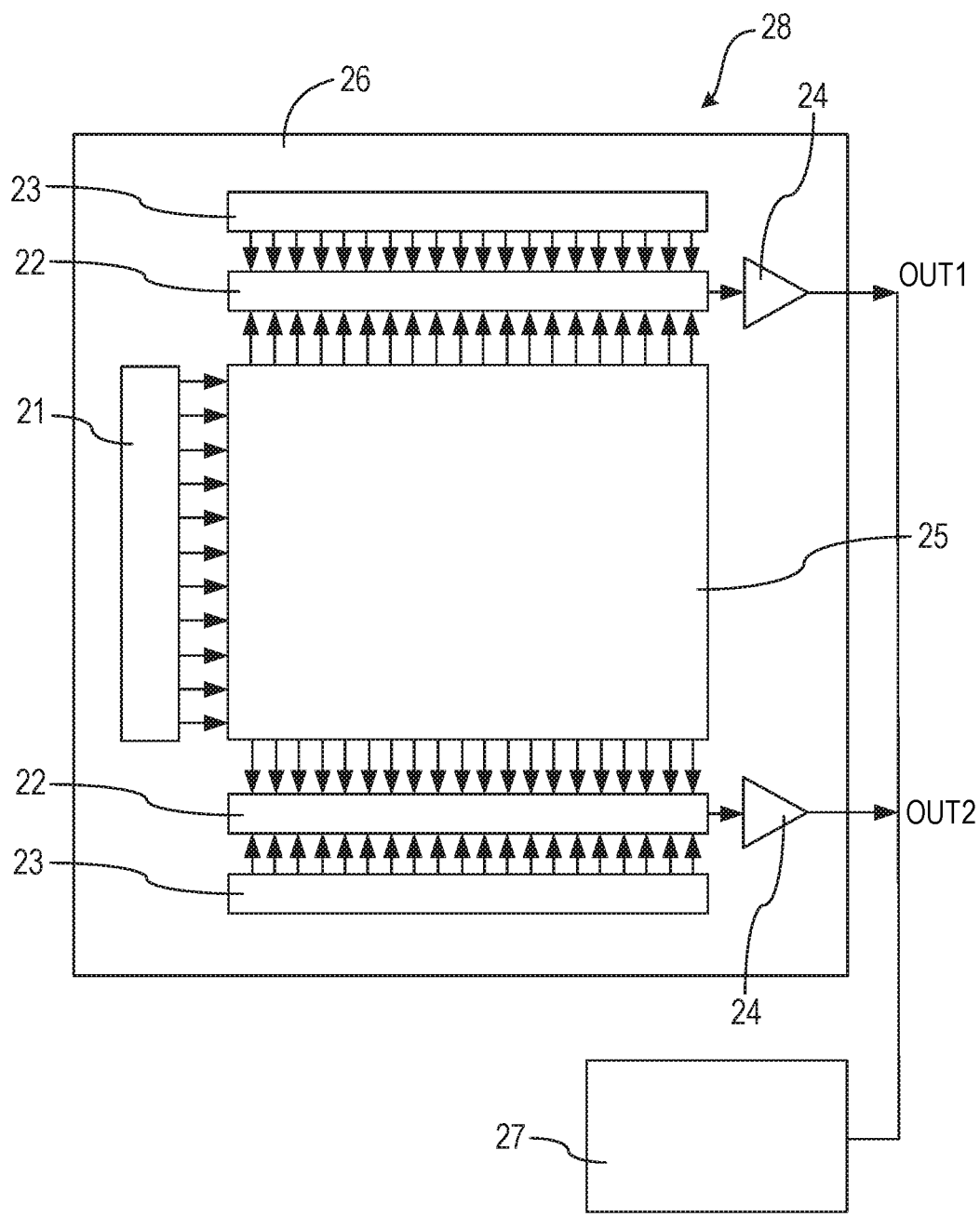
FIG. 3 is a schematic view for illustrating an imaging device according to one embodiment.

FIG. 3 is a schematic view for illustrating the imaging device according to the embodiment. An imaging device 28 includes an imaging region 25 in which a plurality of pixels are arranged in a two-dimensional manner, and a peripheral region 26. The region except the imaging region 25 is the peripheral region 26. The peripheral region 26 has a vertical scanning circuit 21, readout circuits 22, horizontal scanning circuits 23, and output amplifiers 24, and the output amplifiers 24 are connected to a signal processing portion 27. The signal processing portion 27 is a signal processing portion configured to perform signal processing based on information read out in the readout circuits 22, and examples thereof include a CCD circuit and a CMOS circuit.

Each of the readout circuits 22 includes, for example, a column amplifier, a correlated double sampling (CDS) circuit, and an addition circuit, and performs the amplification, addition, and the like of a signal read out from a pixel in a row selected by the vertical scanning circuit 21 through a vertical signal line. The column amplifier, the CDS circuit, the addition circuit, and the like are arranged in, for example, each pixel column or each plurality of pixel columns. The CDS circuit is a circuit configured to perform CDS signal processing, and performs a kTC noise reduction. The horizontal scanning circuits 23 produce signals for reading out the signals of the readout circuits 22 in order. The output amplifiers 24 amplify and output the signals of columns selected by the horizontal scanning circuits 23.

The foregoing construction is merely a construction example of the imaging device, and the embodiment is not limited thereto. The readout circuits 22, the horizontal scanning circuits 23, and the output amplifiers 24 are vertically arranged one by one across the imaging region 25 in order that two output paths may be formed. However, three or more output paths may be arranged. Signals output from the respective output amplifiers 24 are synthesized as an image signal in the signal processing portion 27.

(2) Imaging Apparatus

The imaging device according to the embodiment can be used in an imaging apparatus. The imaging apparatus includes an imaging optical system having a plurality of lenses, and an imaging device configured to receive light that has passed the imaging optical system. In addition, the imaging apparatus includes an imaging device and a casing configured to store the imaging device, and the casing may have a joining portion capable of being joined to an imaging optical system. The imaging apparatus is more specifically a digital video camera or a digital still camera.

In addition, the imaging apparatus may include a communicating portion configured to allow an image that has been picked up to be viewed from the outside. The communicating portion may include a receiving portion configured to receive a signal from the outside or a transmitting portion configured to transmit information to the outside. The signal received by the receiving portion is a signal configured to control at least one of the imaging range of the imaging apparatus, the start of the imaging thereof, or the end of the imaging. In addition, the transmitting portion may transmit, in addition to the image that has been picked up, information, such as a warning about the image, the remaining amount of a data capacity, and the remaining amount of a power source. When the apparatus includes the receiving portion or the transmitting portion, the apparatus can be used as a network camera.

EXAMPLES

Example 1

(Synthesis of Exemplified Compound A-4)

Exemplified Compound A-4 was synthesized in accordance with a synthesis scheme shown below.

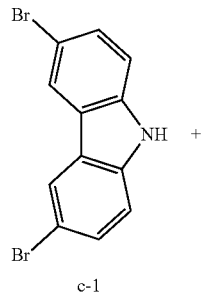

c-1

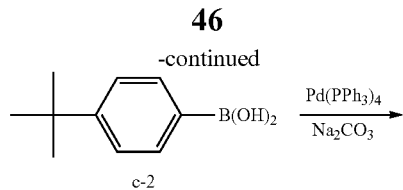

c-2

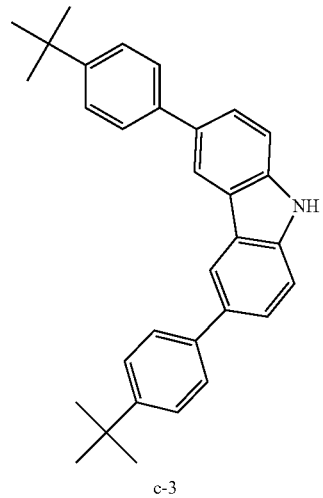

c-3

3.25 Grams (10.0 mmol) of c-1, 5.34 g (30.0 mmol) of c-2, and 7.50 g of sodium carbonate were loaded into a 200-milliliter flask, and 50 ml of toluene, 20 ml of ethanol, and 30 ml of water were loaded into the flask. Further, 347 mg of tetrakistriphenylphosphine palladium was loaded into the flask, and the mixture was heated to reflux and stirred for 6 hours under nitrogen. The reaction liquid was cooled, and was then filtered to provide 2.42 g of c-3 (yield: 56%).

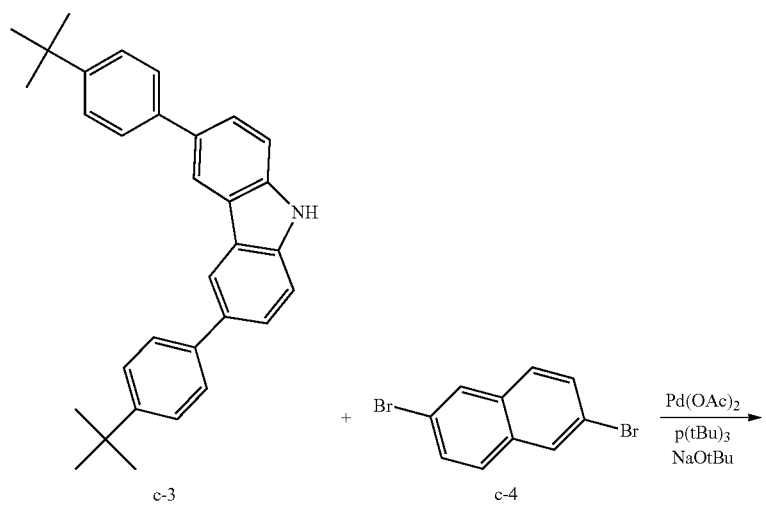

c-3 + c-4

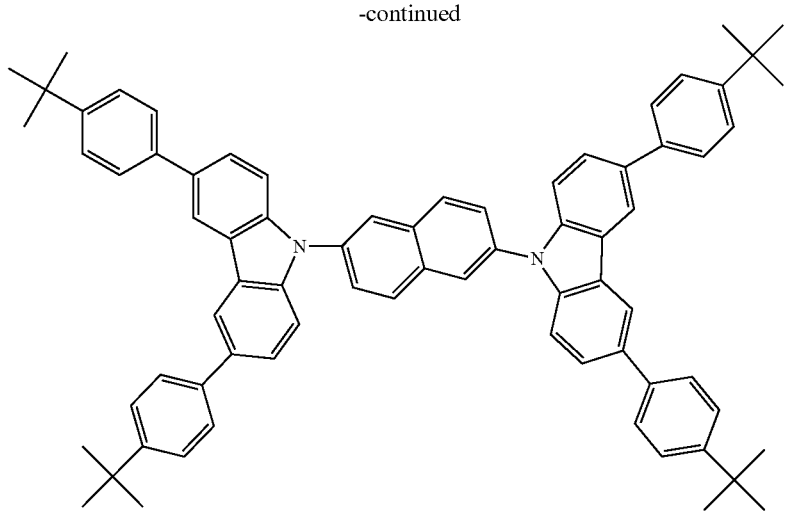

A-4

1.50 Grams (3.48 mmol) of c-3, 0.452 g (1.58 mmol) of c-4, and 0.455 g (4.74 mmol) of sodium tert-butoxide were loaded into a 200-milliliter flask, and 50 ml of xylene was loaded into the flask. Further, 35 mg of palladium acetate and 96 mg of tri-tert-butylphosphine were loaded into the flask, and the mixture was heated to reflux and stirred for 8 hours under nitrogen. The reaction liquid was cooled, and then 50 ml of water was loaded into the liquid, followed by stirring. After that, the mixture was filtered. The crude product was purified by alumina column chromatography (eluent: chloroform/heptane mixture) to provide 0.914 g of Exemplified Compound A-4 (yield: 59%). An m/z of Exemplified Compound A-4 of 987 was identified by mass spectrometry.

Example 2

(Synthesis of Exemplified Compound A-6)

Exemplified Compound A-6 was synthesized in accordance with a synthesis scheme shown below.

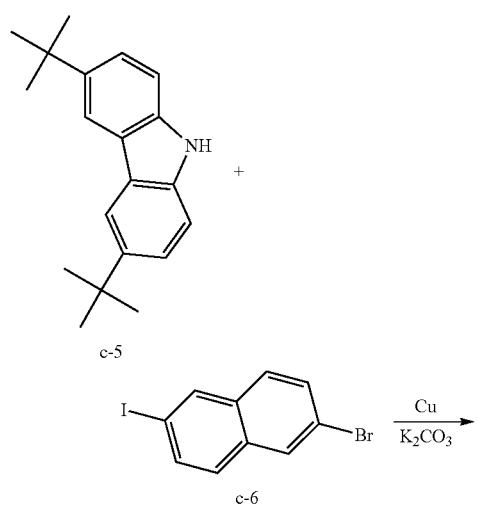

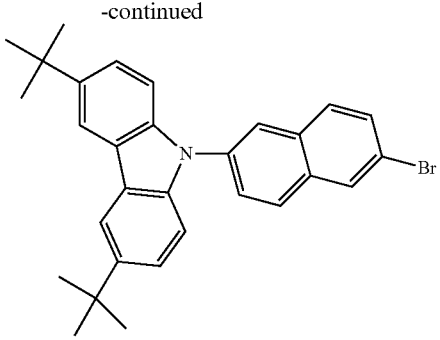

c-7

5.00 Grams (17.9 mmol) of c-5, 7.14 g (21.5 mmol) of c-6, 3.41 g (53.7 mmol) of copper powder, and 3.71 g (26.8 mmol) of potassium carbonate were loaded into a 100-milliliter flask. 50 Milliliters of orthodichlorobenzene was loaded into the flask, and the mixture was heated to reflux and stirred for 6 hours in a nitrogen atmosphere. The reaction liquid was cooled, and was then filtered. The filtrate was concentrated under reduced pressure to provide a crude product. Next, the crude product was purified by silica gel column chromatography (eluent: toluene/heptane mixture) to provide 5.62 g of Compound c-7 (yield: 65%).

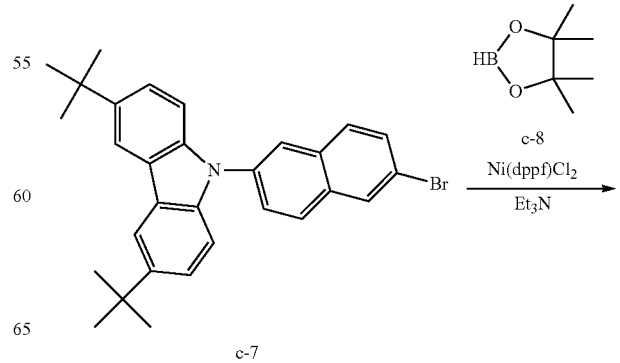

c-7

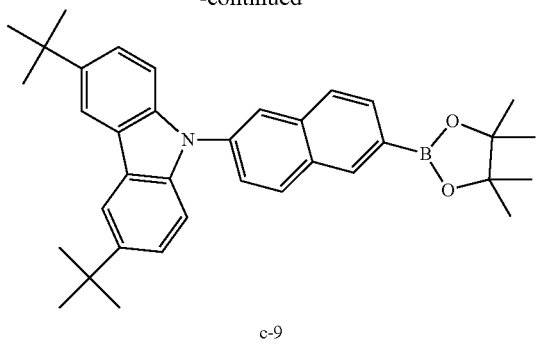

c-9

3.00 Grams (6.20 mmol) of c-7, 424 mg (0.620 mmol) of [1,1'-bis(diphenylphosphino)propane]dichloronickel, 1.60 ml of c-8, 50 ml of toluene, and 10 ml of triethylamine were loaded into a 100-milliliter flask. In a nitrogen atmosphere, the temperature of the mixture was increased to 90° C., and the mixture was stirred for 6 hours. After the reaction, 100 ml of water was added to the resultant. After the reaction, the organic layer was extracted with toluene and dried with anhydrous sodium sulfate, and was then purified with a silica gel column (eluent: toluene/heptane mixture) to provide 2.60 g of c-9 (yield: 79%).

2.60 Grams (4.95 mmol) of c-9, 2.0 g (4.13 mmol) of c-7, 240 mg (0.21 mmol) of tetrakistriphenylphosphine palladium, 1.75 g (16.5 mmol) of sodium carbonate, 60 ml of toluene, 20 ml of ethanol, and 20 ml of water were loaded into a 200-milliliter flask, and the mixture was heated to reflux and stirred for 6 hours in a nitrogen atmosphere. The reaction liquid was cooled, and was then filtered. The resultant solid was dissolved in chlorobenzene under heating, and 40 g of silica gel was loaded into the solution and was dispersed therein at 80° C. The solution was filtered, and the filtrate was concentrated under reduced pressure to provide a crude product. The crude product was recrystallized with toluene to provide 2.17 g of Exemplified Compound A-6 (yield: 65%). An m/z of Exemplified Compound A-6 of 808 was identified by mass spectrometry.

Examples 3 to 8

(Synthesis of Exemplified Compounds)

Exemplified compounds were each synthesized in the same manner as in Example 1 with the exception that in Example 1, the boronic acid raw material (c-2) and the naphthalene raw material (c-4) were changed as shown in Table 4. In addition, the m/z of each of the exemplified compounds was identified by mass spectrometry.

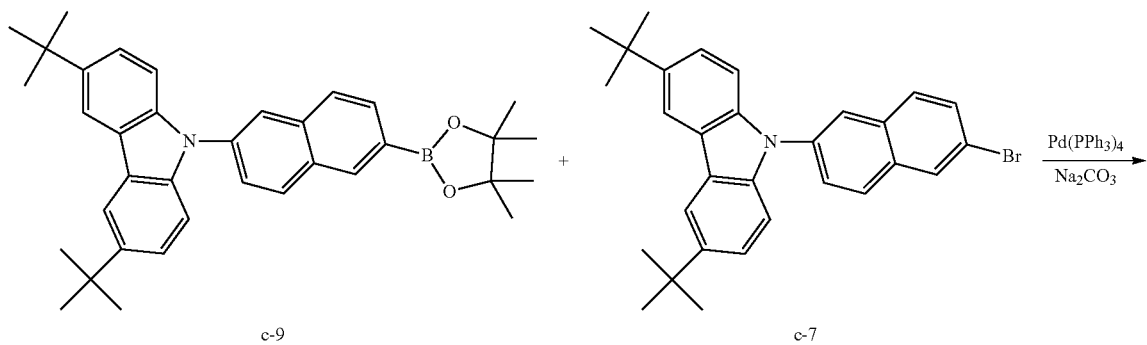

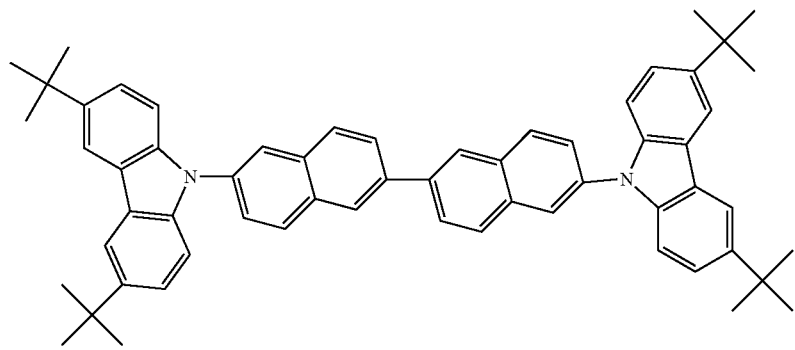

A-6

TABLE 4

| | Boronic acid raw material | Naphthalene raw material | Exemplified Compound No. | m/z identified by mass spectrometry |
|---|---|---|---|---|
| Example 3 | 1-naphthylboronic acid | 2,6-dibromonaphthalene | A-2 | 962 |
| Example 4 | biphenyl-2-boronic acid | 2,7-dibromonaphthalene | A-3 | 1,066 |
| Example 5 | 4-tert-butylphenylboronic acid | 2,7-dibromonaphthalene | B-4 | 987 |
| Example 6 | 4-tert-butylphenylboronic acid | 1,4-dibromonaphthalene | C-4 | 987 |
| Example 7 | 4-tert-butylphenylboronic acid | 1,5-dibromonaphthalene | C-7 | 987 |
| Example 8 | 3,5-di-tert-butylphenylboronic acid | 4,4'-dibromo-1,1'-binaphthyl | C-6 | 1,057 |

Examples 9 and 10

(Synthesis of Exemplified Compounds)

Exemplified compounds were each synthesized in the same manner as in Example 2 with the exception that in Example 2, the carbazole raw material (c-5) and the naphthalene raw material (c-6) were changed as shown in Table 5. In addition, the m/z of each of the exemplified compounds was identified by mass spectrometry.

TABLE 5

| | Carbazole raw material | Naphthalene raw material | Exemplified Compound No. | m/z identified by mass spectrometry |
|---|---|---|---|---|
| Example 9 | 3,6-diphenyl-9H-carbazole | 2-iodo-6-bromonaphthalene | A-1 | 888 |
| Example 10 | 3-(3,5-di-tert-butylphenyl)-9H-carbazole | 2-iodo-6-bromonaphthalene | A-5 | 961 |

Example 11

(Production of Photoelectric Conversion Element)

A photoelectric conversion element in which the hole-collecting electrode (cathode) 4, the electron-blocking layer (second organic layer) 2, the photoelectric conversion layer (first organic layer) 1, the hole-blocking layer (third organic layer) 3, and the electron-collecting electrode (anode) 5 were sequentially formed on a substrate was produced by a method to be described below.

First, an indium zinc oxide film was formed on a Si substrate. After that, the film was subjected to patterning processing so as to have a desired shape. Thus, the hole-collecting electrode 4 was formed. At this time, the thickness of the hole-collecting electrode 4 was set to 100 nm. The substrate on which the hole-collecting electrode 4 had been formed as described above was used as a substrate with an electrode in the next process.

Next, organic compound layers (the electron-blocking layer 2, the photoelectric conversion layer 1, and the hole-blocking layer 3) and an electrode layer (the electron-collecting electrode 5) shown in Table 6 were continuously formed on the substrate with an electrode. The photoelectric conversion layer 1 was produced by co-deposition, and a mixing ratio between its constituent materials is as shown in Table 6. At this time, the electrode area of the opposing electrode (the electron-collecting electrode 5) was set to 3 mm2. After that, the protective layer 7 was formed from SiN. Further, the produced element was subjected to an annealing treatment by being left at rest under air on a hot plate at 170° C. for 30 minutes.

TABLE 6

| | Constituent material | Thickness (nm) |
|---|---|---|
| Electron-blocking layer | Exemplified Compound A-4 | 100 |
| Photoelectric conversion layer | CG6:CG25 = 50:50 (mass ratio) | 400 |
| Hole-blocking layer | Fullerene C60 | 50 |
| Electron-collecting electrode | Indium zinc oxide | 30 |

Examples 12 to 18 and Comparative Example 1

(Production of Photoelectric Conversion Elements)
Photoelectric conversion elements were each produced by the same method as that of Example 11 with the exception that in Example 11, the electron-blocking layer was appropriately changed as shown in Table 7.

TABLE 7

| | Electron-blocking layer |
|---|---|
| Example 12 | Exemplified Compound A-6 |
| Example 13 | Exemplified Compound A-3 |
| Example 14 | Exemplified Compound B-4 |
| Example 15 | Exemplified Compound A-5 |
| Example 16 | Exemplified Compound C-4 |
| Example 17 | Exemplified Compound C-7 |
| Example 18 | Exemplified Compound C-6 |
| Comparative Example 1 | Comparative Compound a-1 |

[Evaluation of Characteristics of Photoelectric Conversion Element]
The characteristics of the photoelectric conversion elements obtained in Examples and Comparative Examples were measured and evaluated.

(1) Current Characteristic
A current flowing through an element at the time of the application of a voltage of 5 V to the element was observed. As a result, in each of the photoelectric conversion elements produced in Examples, a ratio ((current in bright place)/(current in dark place)) between a current in a bright place and a current in a dark place was 100 times or more. Accordingly, it was confirmed that the photoelectric conversion elements produced in Examples each functioned well.

(2) Quantum Yield (External Quantum Efficiency) and Dark Current
External quantum efficiency was calculated by measuring the density of a photocurrent flowing through each element when the element was irradiated with monochromatic light having a wavelength of 550 nm and an intensity of 50 μW/cm2 under a state in which a voltage of 5 V was applied between the hole-collecting electrode 4 and electron-collecting electrode 5 of the element. The photocurrent density was determined by subtracting a dark current density at the time of light shielding from a current density at the time of the light irradiation. The monochromatic light used in the measurement is obtained by monochromatizing white light output from a xenon lamp (apparatus name: XB-50101AA-A (product name), manufactured by Ushio Inc.) with a monochromator (apparatus name: MC-10N (product name), manufactured by Ritu Oyo Kougaku Co., Ltd.). The application of the voltage to the element and the current measurement were performed with a source meter (apparatus name: R6243 (product name), manufactured by Advantest Corporation). In addition, the light was caused to enter vertically to the element and from an upper electrode (electron-collecting electrode 5) side.

With regard to a dark current, a dark current (current density when an element was left at rest in a dark place) was measured under a state in which a voltage of 5 V was applied between the hole-collecting electrode 4 and the electron-collecting electrode 5.

A relative value for external quantum efficiency when the external quantum efficiency of the photoelectric conversion element of Example 11 was defined as 1 was evaluated by the following criteria. The results are shown in Table 8.

○: A case in which the relative value for the external quantum efficiency is 0.9 or more
×: A case in which the relative value for the external quantum efficiency is less than 0.9

A relative value for a dark current when the dark current of the photoelectric conversion element of Example 11 was defined as 1 was evaluated by the following criteria. The results are shown in Table 8.

TABLE 8

| | External quantum efficiency | Dark current |
|---|---|---|
| Example 12 | ○ | □ |
| Example 13 | ○ | ○ |
| Example 14 | ○ | □ |
| Example 15 | ○ | ○ |
| Example 16 | ○ | ○ |
| Example 17 | ○ | ○ |
| Example 18 | ○ | ○ |
| Comparative Example 1 | × | × |

□: A case in which the relative value for the dark current is 0.1 or more and less than 1
○: A case in which the relative value for the dark current is 1 or more and less than 10
×: A case in which the relative value for the dark current is 30 or more As described above in Examples, it has been found that when the organic compound of the present invention is incorporated into an electron-blocking layer, a dark current in a photoelectric conversion element can be reduced, and a high-efficiency photoelectric conversion element can be provided. According to the present invention, there can be provided an organic compound that is excellent in sublimability, that has a high glass transition temperature, that can form a highly amorphous layer, and that can be suitably used in the organic compound layer of a photoelectric conversion element.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:
1. An organic compound represented by formula [1]:

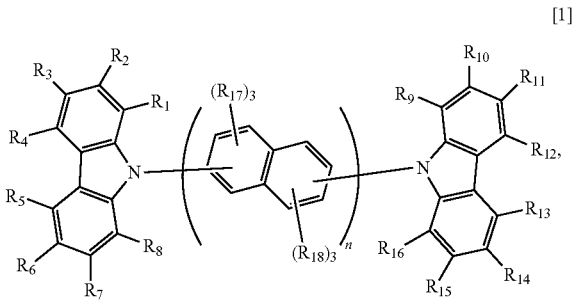

wherein each of $R_1$ to $R_{18}$ represents a hydrogen atom, a substituted or unsubstituted alkyl group, a substituted or unsubstituted aromatic hydrocarbon group, or a substituted or unsubstituted aromatic heterocyclic group, and can be identical to or different from each other, and plurality of $R_{17}$'s or plurality of $R_{18}$'s can be identical to or different from each other, wherein at least one of the $R_3$, the $R_6$, the $R_{11}$, and the $R_{14}$ represents the alkyl group or the aromatic hydrocarbon group, wherein n represents an integer of 1 to 3, and each naphthalene skeleton of each naphthalene unit bonds to an adjacent naphthalene or carbazole skeleton at 2,6- or 2,7-positions, and wherein when the n represents 2 or more, naphthalene units can be identical to or different from each other.

2. The organic compound according to claim 1, wherein the at least one of the $R_3$, the $R_6$, the $R_{11}$, and the $R_{14}$ is selected from the group consisting of an iso-propyl group, a sec-butyl group, a tert-butyl group, a 4-iso-propylphenyl group, a 4-sec-butylphenyl group, and a 4-tert-butylphenyl group.

3. The organic compound according to claim 1, the aromatic hydrocarbon group represents a 4-iso-propylphenyl group, a 4-sec-butylphenyl group, or a 4-tert-butylphenyl group.

4. An organic device comprising:
an anode;
a cathode; and
an organic compound layer arranged between the anode and the cathode,
wherein the organic compound layer has a layer containing the organic compound according to claim 1.

5. The organic device according to claim 4, wherein the organic compound layer has a photoelectric conversion layer, and an electron-blocking layer arranged between the photoelectric conversion layer and the cathode, and the layer containing the organic compound comprises the electron-blocking layer.

6. The organic device according to claim 5, wherein the electron-blocking layer is in contact with the cathode.

7. The organic device according to claim 5, wherein the photoelectric conversion layer contains one of a fullerene, a fullerene analog, and a fullerene derivative.

8. The organic device according to claim 4, further comprising a hole-blocking layer between the anode and the organic compound layer, wherein the hole-blocking layer contains one of a fullerene, a fullerene analog, and a fullerene derivative.

9. A photoelectric conversion apparatus comprising a plurality of kinds of photoelectric conversion elements configured to receive light beams having different wavelengths,
wherein at least one kind of photoelectric conversion element out of the plurality of kinds of photoelectric conversion elements comprises the organic device of claim 4, and
wherein a plurality of kinds of organic devices are laminated.

10. An imaging device comprising:
the organic device of claim 4;
a readout circuit connected to the organic device; and
a signal processing circuit connected to the readout circuit.

11. An imaging apparatus comprising:
an imaging optical system; and
an imaging device configured to receive light that has passed the imaging optical system,
wherein the imaging device comprises the imaging device of claim 10.

12. An imaging apparatus comprising:
the imaging device of claim 10; and
a casing configured to store the imaging device,
wherein the casing has a joining portion capable of being joined to an imaging optical system.

13. The imaging apparatus according to claim 12, further comprising a receiving portion configured to receive a signal from an outside,
wherein the signal comprises a signal configured to control at least one of an imaging range of the imaging apparatus, a start of imaging thereof, or an end of the imaging.

14. The imaging apparatus according to claim 13, further comprising a transmitting portion configured to transmit an acquired image to an outside.

15. An organic device comprising:
an anode;
a cathode; and
an organic compound layer arranged between the anode and the cathode,
wherein the organic compound layer has a layer containing an organic compound represented by formula [1]:

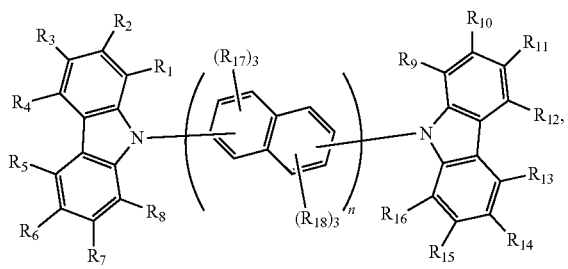

[1]

wherein each of $R_1$ to $R_{18}$ represents a hydrogen atom, a substituted or unsubstituted alkyl group, a substituted or unsubstituted aromatic hydrocarbon group, or a substituted or unsubstituted aromatic heterocyclic group, and can be identical to or different from each other, and plurality of $R_{17}$'s or plurality of $R_{18}$'s can be identical to or different from each other, wherein at least one of the $R_3$, the $R_6$, the $R_{11}$, and the $R_{14}$ represents the alkyl group or the aromatic hydrocarbon group, wherein the aromatic hydrocarbon group represents a 4-iso-propylphenyl group, a 4-sec-butylphenyl group, or a 4-tert-butylphenyl group, and wherein n represents an integer of 1 to 3, and when the n represents 2 or more, naphthalene units can be identical to or different from each other, and bonding positions of the naphthalene units with adjacent groups can be identical to or different from each other.

16. A photoelectric conversion element comprising:
an anode;
a cathode; and
an organic compound layer arranged between the anode and the cathode,
wherein the organic compound layer has a layer containing an organic compound represented by formula [1]:

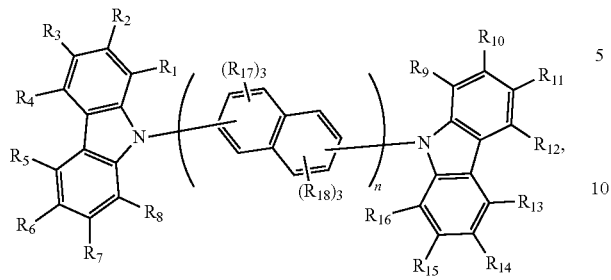

[1]

wherein each of $R_1$ to $R_{18}$ represents a hydrogen atom, a substituted or unsubstituted alkyl group, a substituted or unsubstituted aromatic hydrocarbon group, or a substituted or unsubstituted aromatic heterocyclic group, and can be identical to or different from each other, and plurality of $R_{17}$'s or plurality of $R_{18}$'s can be identical to or different from each other, wherein at least one of the $R_3$, the $R_6$, the $R_{11}$, and the $R_{14}$ represents the alkyl group or the aromatic hydrocarbon group, wherein n represents an integer of 1 to 3, and each naphthalene skeleton of each naphthalene unit bonds to an adjacent naphthalene or carbazole skeleton at 2,6- or 2,7-positions, and wherein when the n represents 2 or more, naphthalene units can be identical to or different from each other.

\* \* \* \* \*